(12) United States Patent
Brennan et al.

(10) Patent No.: US 7,390,630 B1
(45) Date of Patent: Jun. 24, 2008

(54) METHOD OF IDENTIFYING A COMPOUND THAT SELECTIVELY INHIBITS CYTOKINE-STIMULATED T CELL INDUCED PRODUCTION OF TNF-ALPHA BY MONOCYTES

(75) Inventors: Fionula Mary Brennan, London (GB); Marc Feldmann, London (GB); Brian Maurice John Foxwell, London (GB)

(73) Assignee: Mathilda and Terence Kennedy Institute of Rheumatology Trust, London (GB)

( * ) Notice: Subject to any disclaimer, the term of this patent is extended or adjusted under 35 U.S.C. 154(b) by 636 days.

(21) Appl. No.: 10/088,801

(22) PCT Filed: Sep. 25, 2000

(86) PCT No.: PCT/GB00/03660

§ 371 (c)(1),
(2), (4) Date: Sep. 18, 2002

(87) PCT Pub. No.: WO01/21202

PCT Pub. Date: Mar. 29, 2001

(30) Foreign Application Priority Data

Sep. 24, 1999 (GB) ................................. 9922505.4

(51) Int. Cl.
*G01N 33/53* (2006.01)
(52) U.S. Cl. ..................................... 435/7.24; 435/40.5
(58) Field of Classification Search ........................ None
See application file for complete search history.

(56) References Cited

U.S. PATENT DOCUMENTS 5,085,985 A    2/1992   Maino et al.

FOREIGN PATENT DOCUMENTS

EP           0896 999 A1    3/1997

OTHER PUBLICATIONS

Sebbag et.al. Cytokine stimulation of t lymphocytes regulates their capacity to induce monocyte . . . rheumatoid arthritis. Eur. J. Immunol. 1997; 27: 624-632.*
Parry et.al. Contact with T cells modulates monocyte IL-10 production. The Journal of Immunology. 1997; 158: 3673-3681.*
Foxwell et al, Proc Nat'l Acad Sci USA, *Efficient Adenoviral Infection with IkBa Reveals that Macrophage Tumor Necrosis Factor a Production in Rheumatoid Arthritis is NF-kB Dependent*, vol. 95, Jul. 1998, pp. 8211-8215.
Eigler et al, Immunology Today, *Taming TNF: Strategies to Restrain this Proinflammatory Cytokine*, vol. 18, (1997), pp. 487-492.
Sebbag et al, Eur J Immunology, *Cytokine Stimulation of T Lymphocytes Regulates Their Capacity to Induce Monocyte Production of tumor Necrosis Factor-α, but not Interleukin-10: Possible Revlevance to Pathophysiology of Rheumatoid Arthritis*, vol. 27, (1997), pp. 624-632.
Ward et al, Immunology Today, *PI 3-Kinase: a Pivotal Pathway in T-Cell Activation?*, vol. 17, (1996) pp. 187-197.
Bhattacharyya et al, J Leucocyte Biology, *Activated T Lymphocytes Induce Degranulation and Cytokine Production by Human Mast Cells Following Cell-To-Cell Contact*, vol. 63, (1998), pp. 337-341.
Chabot et al, J Clin Invest, *Microglial Production of TNF-α Is Induced by Activated Lymphocytes*, vol. 100, (1997), pp. 604-612.
Avice et al, J Immunology, *Lymphocyte Activation Gene-3, a MHC Class II Ligand Expressed on Activated T Cells, Stimulates TNF-α and IL-12 Produciton by Monocytes and Dendritic Cells*, vol. 162, (1999), pp. 2748-2753.
MacLean et al., Journal of Immunology, *Anti-CD3:Anti-IL-2 Receptor Bispecific Monoclonal Antibody*, vol. 150, No. 4, Feb. 15, 1993, pp. 1619-1628.
Londei et al, Symposium on Molecular and Cellular Mechanisms of Human Hypersensitivity and Autoimmunity Held at the 17th Annual UCLA Symposia on Molecular and Cellular Biology, *Cloning of Activated T Cells From Rheumatoid Arthritis Joints: Detection of Collagen type II Specific Cells*, (1988) Abstract.
Cohen et al, Arthritis and Rheumatism, *High Level of Interleukin-10 Production by the Activated T Cell Population Within the Rheumatoid Synovial Membrane*, vol. 38, No. 7, Jul. 1995, pp. 946-952.
Bondeson et al, Proc. Natl. Acad. Sci USA, *Defining Therapeutic Targets by Using Adenovirus: Blocking NF-kB Inhibits Both Inflammatory and Destructive Mechanisms in Rheumatoid Synovium but Spares Anti-Inflammatory Mediators*, vol. 96, (1999) pp. 5668-5673.
Carson, Nature Medicine, *Unconventional T-Cell Activation by IL-15 in Rheumatoid Arthritis*, vol. 3, (1997), pp. 148-149.
McInnes et al, Nature Medicine, *Interleukin-15 Mediates T Cell-Dependent Regulation of Tumor Necrosis Factor-α Production in Rheumatoid Arthritis*, vol. 3, (1997), pp. 189-195.
Yocum, Seminars in Arthritis and Rheumatism, *T Cells: Pathogenic Cells and Therapeutic Targets in Rheumatoid Arthritis*, vol. 29, (1999), pp. 27-35.

(Continued)

*Primary Examiner*—Eileen B. O'Hara
*Assistant Examiner*—Zachary Skelding
(74) *Attorney, Agent, or Firm*—Nikolai & Mersereau, P.A.; C. G. Mersereau

(57) ABSTRACT

A method of identifying a compound with efficacy in the treatment of chronic inflammatory disease by testing the compound for an ability to selectively inhibit the ability of $T_{ck}$ cells to induce pro-inflammatory cytokine release from a monocyte is disclosed. The method includes pre-incubatin $T_{ck}$ cells with a compound to be tested, optionally resuspending the $T_{ck}$ cells in the absence of the test compound, co-culturing the $T_{ck}$ cells with monocytes, and assaying for the production of pro-inflammatory cytokines by the monocytes. The $T_{ck}$ cells are produced by incubating a population of T cells with one or more cytokines or the $T_{ck}$ cells are isolated from synovial tissue. The $T_{ck}$ cells have not been contacted with an anti-CD3 antibody. The ability to selectively inhibit cytokine release indicates that the compound has efficacy in the treatment of chronic inflammatory disease.

4 Claims, 9 Drawing Sheets

OTHER PUBLICATIONS

Figure 1:
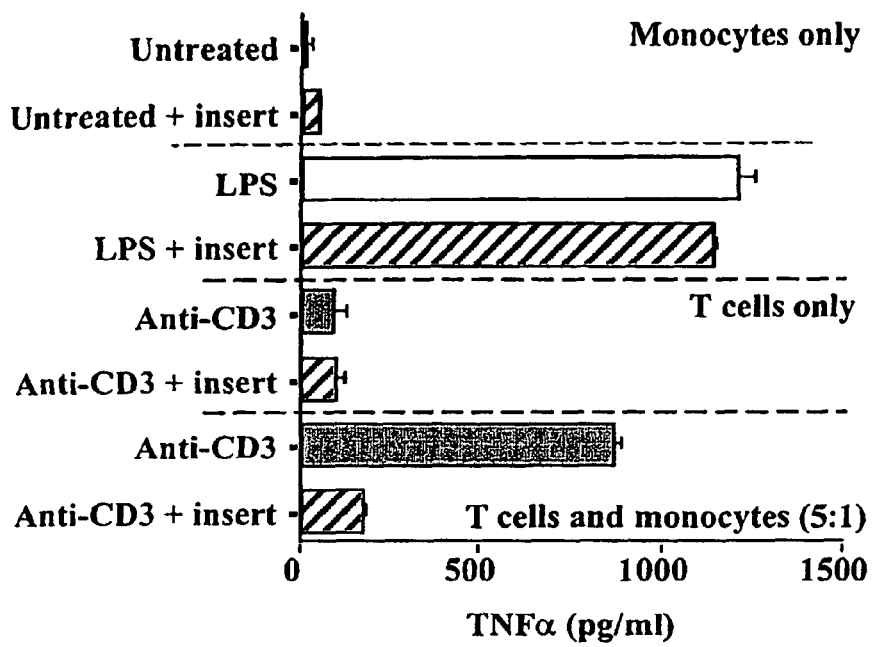
Figure 1:
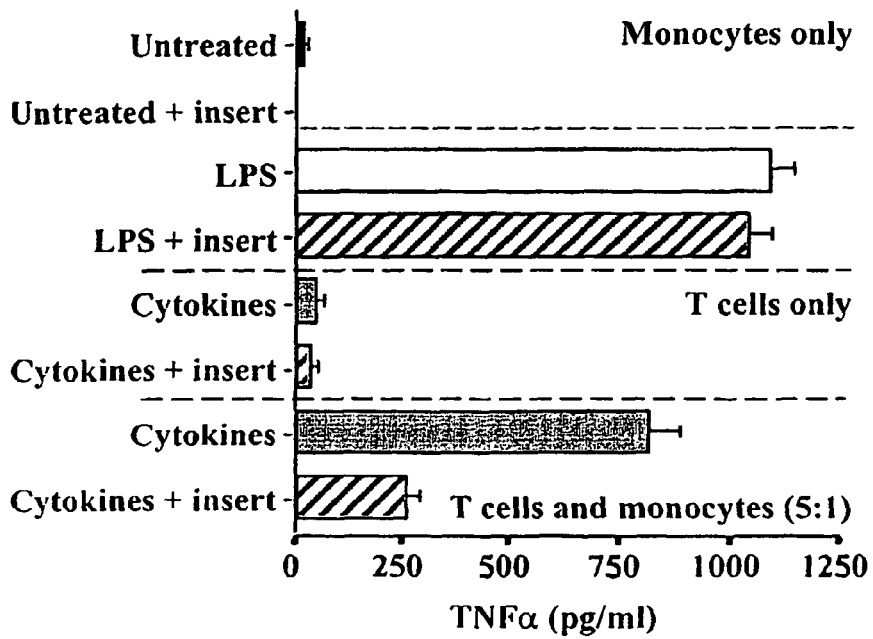

Crawley et al., Journal of Biological Chemistry, *Interleukin-10 Stimulation of Phosphatidylinositol 3-Kinase and p70 S6 Kinase is Required for the Proliferative but not the Antiinflammatory Effects of the Cytokine*, vol. 271, No. 27, Jul. 5, 1996, pp. 16357-16362.

Clarke et al, Eur. Journal of Immunology, *Interleukin-4 Inhibits X Light Chain Expression and NFxB Activation but not IxBa Degradation in 70Z/3 Murine Pre-B Cells*, vol. 25, (1995) pp. 2961-2966.

McInnes et al, Immunology Today, *Interleukin 15: A Proinflammatory Role in Rheumatoid Arthritis Synovitis*, (1998) vol. 19, pp. 75-79.

Shah et al, Nature Medicine, *A Role for IL-15 in Rheumatoid Arthritis*, (1998) vol. 4, p. 643.

Yoshizaki et al, Springer Semin Immunopathol, Therapy of Rheumatoid Arthritis by Blocking IL-6 Signal Transduction with a Humanized Anti-IL-6 Receptor Antibody, vol. 20, 1998, pp. 247-259.

Helfrich et al, Int. J. Cancer, Construction and Characterization of a Bispecific Diabody for Retargeting T Cells to Human Carcinomas, vol. 76, 1998, pp. 232-239.

Contreras et al, Transplantation, Peritransplant Tolerance Induction With Anti-CD3-Immunotoxin, vol. 65, No. 9, May 15, 1998, pp. 1159-1169.

Faherty et al, The Journal of Immunology, Failure of IL-1 Receptor Antagonist and Monoclonal Anti-IL-1 Receptor Antibody to Inhibit Antigen-Specific Immune Responses In Vivo, vol. 148, No. 3, Feb. 1, 1992 pp. 766-771 (All References Previously Submitted).

\* cited by examiner

METHOD OF IDENTIFYING A COMPOUND THAT SELECTIVELY INHIBITS CYTOKINE-STIMULATED T CELL INDUCED PRODUCTION OF TNF-ALPHA BY MONOCYTES

The present application is a 371 of co-pending application PCT/GB00/03660 having an international filing date of 25 Sep. 2000 and a priority date of 24 Sep. 1999.

FIELD OF THE INVENTION

The present invention relates to methods of treatment of chronic inflammatory diseases and compounds and antibodies for use in the same. In particular, the present invention relates to methods of identifying a compound with efficacy in the treatment of a chronic inflammatory disease.

BACKGROUND TO THE INVENTION

Chronic inflammatory diseases, such as rheumatoid arthritis, Crohn's disease, multiple sclerosis and atherosclerosis, are diseases in which the body's immune system produces anti-self (ie. autoimmune) responses. In the case of rheumatoid arthritis, the clinical syndrome is characterised by relapsing/remitting inflammation within the synovial membrane, associated with progressive, erosive destruction of adjacent cartilage and bone. On a cellular level, these events are coincident with chronic infiltration of the synovial membrane with T cells, plasma cells and macrophages.

There is mounting evidence to implicate T cells in the initiation and perpetuation of chronic inflammatory diseases such as rheumatoid arthritis (RA). For example, patients with RA have been found to carry a specific polymorphism in the class II major histocompatibility complex (MHC), which is believed to render them genetically predisposed to developing RA (Panayi et al., 1992, *Arthritis Rheum.* 35:729-735). A key function of class II MHC is to present antigen to a subpopulation of T cells, termed T helper cells, which are characterised by CD4+ surface markers. It is proposed that antigen presentation results in clonal expansion and activation of this population of T cells, which in turn leads to stimulation of other populations of synovial cells, such as macrophages, and the consequent release of pro-inflammatory cytokines. To date, however, the nature of the environmental stimulus that triggers RA remains unknown.

In addition to a role in initiation of RA, T helper cells are also proposed to be important in the perpetuation of this disease, either by becoming activated against self-proteins (e.g. peptides derived from the degradation of MHC molecules and/or structural proteins in the joint) or by being re-exposed to the initiating antigen. This further activation of T cells is suggested to result in the sustained release of pro-inflammatory cytokines, as well as enzymes that mediate destruction of the cartilage and bone.

As a consequence of the growing evidence of an involvement of T cells in the pathogenesis of RA, several treatments of this disease have been developed which target T cells via their surface markers, for example anti-CD4 antibody therapy, anti-CD52 antibody therapy, anti-CD5 antibody therapy and anti-interleukin-2 receptor antibody therapy (e.g. van der Lubbe et al., 1995, *Arthritis Rheum.* 38:1097-1106; Weinblatt et al., 1995, *Arthritis Rheum.* 38:1589-1594; Olsen et al, 1996, *Arthritis Rheum.* 39:1102-1108; Moreland et al., 1995, *Arthritis Rheum.* 38:1177-1186). However, the results of clinical trials with such therapies have been largely disappointing, as a result of a lack of efficacy and/or the presentation of toxicity-related side effects. These limitations are thought to be due, at least in part, to the lack of specificity of the therapies for the particular population of T cells responsible for inducing production of pro-inflammatory cytokines by macrophages in RA joints.

An alternative approach for developing new treatments of RA has been to target the pro-inflammatory cytokines produced in the synovium by macrophages in response to T cell activation. Although several different pro-inflammatory cytokines may be released from macrophages following T cell activation in RA tumour necrosis factor α (TNFα) has attracted particular attention. The importance of TNFα was initially demonstrated using dissociated rheumatoid joint cell cultures (Brennan et al., 1989, *Lancet* 2(8657): 244-247) and subsequently confirmed in animal models of arthritis (Thorbecke et al., 1992, *Proc. Natl. Sci. USA* 89:7375-7379; Williams et al., 1992, *Proc. Natl. Sci. USA* 89:9784-9788). The findings of these pre-clinical studies led to successful clinical trials of anti-TNFα antibody therapy, establishing the importance of TNFα as a therapeutic target (e.g. Elliott et al., 1993, *Arthritis Rheum.* 36:1681-1690; Elliott et al., 1994, *Lancet* 344:1105-1110; Elliott et al., 1994, *Lancet* 344:1125-1127).

In RA joints, the cells responsible for the majority of TNFα production are macrophages (Chu et al., 1991, *Arthritis Rheum.* 34:1125-1132). Hence, there is much interest in understanding the mechanisms underlying the regulation of TNFα production in cells of this lineage. Available data suggest that both water-soluble factors and cell-cell interactions may be involved in mediating T cell-induced production of TNFα by macrophages/monocytes.

Sebbag et al. (1997) *Eur. J. Immunol.* 27:624-632 recently demonstrated that cytokine stimulation (using IL-15 alone, or a cocktail of IL-6, TNFα and IL-2) could activate a specific subset of T helper cells termed cytokine stimulated T cells or '$T_{ck}$ cells' (formerly '$T_{cy}$ cells'), which in turn could induce TNFα production (but not IL-10 production) in monocytes. Stimulation of conventional T cell receptor-stimulated T cells ('$T_{tcr}$ cells') using anti-CD3 antibodies also induced TNFα production by monocytes, in addition to the production of an anti-inflammatory cytokine, IL-10 (Parry et al., 1997, *J. Immunol.* 158:3673-3681). In the case of both $T_{ck}$ and $T_{tcr}$ cell stimulation, TNFα production was found to be dependent on cell-cell interactions between T cells and macrophages. On the basis of these findings, Sebbag et al. postulated that $T_{ck}$ cells might contribute to the production of pro-inflammatory cytokines in RA synovial tissue, thus contributing to the relative imbalance of pro-inflammatory cytokines (e.g. TNFα) over anti-inflammatory cytokines (e.g. IL-10) in such tissue.

Interleukin-15 (IL-15) has also been implicated in the production of TNFα in RA. This pro-inflammatory cytokine, known to be present in RA synovium (McInnes et al, 1996, *Nature Medicine* 2:175-182), has been shown to activate peripheral blood T cells which, in turn, are able to induce TNFα production in U937 cells and adherent RA synovial cells in a contact-dependent manner (McInnes et al, 1997, *Nature Medicine* 3(2): 189-195).

To date, however, the identity of the T cell population(s) that mediate(s) the production of pro-inflammatory cytokines in RA synovial tissue remains unclear. Furthermore, a means of selectively targeting such cells is absent. Hence, the present invention seeks to provide a method of identifying compounds with efficacy in the treatment of a chronic inflammatory disease, for example compounds which selectively target, either directly or indirectly via cytokine-stimulated T cells, macrophages/monocytes responsible for the production of pro-inflammatory cytokines in RA synovial tissue.

SUMMARY OF THE INVENTION

A first aspect of the present invention provides a method of treatment of a chronic inflammatory disease in a patient, the method comprising the administration to the patient of a compound that selectively inhibits $T_{ck}$ cells.

By "$T_{ck}$ cells" we mean T cells activated by one or more cytokines. Typically, $T_{ck}$ cells are made by activation by prolonged incubation (e.g. for 8 days) with a single cytokine (e.g. IL-15) or a cocktail of cytokines (e.g. IL-6, TNFα and either IL-2 or IL-15).

By "selectively inhibits" we mean an ability to inhibit, either directly or indirectly, $T_{ck}$ cell-induced activation of monocytes to a greater extent than activation by other T cell populations, such as $T_{tcr}$ cells. The inhibition may leave the $T_{ck}$ population intact (but functionally inhibited) or it may reduce the number of $T_{ck}$ cells present, for example by selectively killing them. The compound may alternatively act on the monocytes, before or after activation by the $T_{ck}$ cells, in order to reduce the formation and/or release of cytokines by those monocytes. Preferably, the inhibitory effect of the compound on $T_{ck}$ cell-induced activation of monocytes is at least twice that on $T_{tcr}$ cell-induced activation. More preferably, the compound inhibits $T_{ck}$ cell-induced activation at least three, four, five or ten times more than it inhibits $T_{tcr}$ cell-induced activation. Most preferably, the compound inhibits $T_{ck}$ cell-induced activation but does not substantially inhibit $T_{tcr}$ cell-induced activation.

By "$T_{tcr}$ cells" we mean T cells activated by triggering of the T cell receptor for antigen on T cells. For example, $T_{tcr}$ cells may be produced by incubating T cells with antigen plus antigen-presenting cells, with antibodies to the T cell receptor (such as anti-CD3 antibodies), or with mitogens (such as PHA) which activate T cell receptors.

In a preferred embodiment, said compound selectively inhibits $T_{ck}$ cell-induced release of one or more pro-inflammatory cytokines from monocytes. Preferably, the cytokine is tumour necrosis factor-α.

Conveniently, said compound selectively inhibits NF-κB.

Advantageously, said compound selectively activates PI3 kinase.

In a preferred embodiment of the first aspect of the invention, gene therapy systems may be employed, such as the model adenovirus-based AdvIκBα system disclosed herein, to introduce polynucleotides encoding molecules which selectively inhibit $T_{ck}$ cells. For example, the compound that selectively inhibits $T_{ck}$ cells may comprise a nucleic acid molecule (e.g. cDNA or mRNA) encoding the NF-κB inhibitor, IκBα, said compound being delivered into target cells (such as macrophages and lymphocytes in the synovium) whereupon it is expressed to produce an active IκcBα protein.

Such gene therapy approaches may be used to inhibit $T_{ck}$ cell-induced release of proinflammatory cytokines from monocytes target $T_{ck}$ cells either by targeting the $T_{ck}$ cells or by targeting monocytes. Selectivity may be enhanced by the incorporation of a target cell-specific promoter in the vector.

An exemplary T cell specific promoter is the CD2 promoter (Zhumabekov et al, 1995, *J. Immunol. Methods* 185:133-40).

It will be appreciated by persons skilled in the art that any of the methods of gene therapy known in the art may be utilised (for reviews see Lemoine and Cooper (Eds.), 1996, *Gene Therapy*, BIOS Science Publications; Scientific American, June 1997, Special Edition on Gene Therapy pp 79-103; Rosenberg (Ed.), 2000, *'Principles Practice of Gene Therapy'*, In: *Biologic Therapy of Cancer*, pp 733-823, Lippincot Williams and Wilkins).

For example, viral vectors such as those based on retroviruses (Kuriyama et al, 1991, *Cell Struc. and Func.* 16, 503-510; Culver et al, 1992, *Science* 256, 1550-1552; Miller & Vile, 1995, *FASEB J.* 9, 190-199), adenoviruses (Curiel, 1993, *Prog. Med. Virol.* 40, 1-18; Wagner et al, 1990, *Proc. Natl. Acad. Sci. USA* 87, 3410-3414; Cotten et al (1992) *Proc. Natl. Acad. Sci. USA* 89, 6094-6098; WO 94/10323; Michael et al, 1995, *Gene Therapy* 2, 660-668; Bischoff et al, 1996, *Science* 274, 373-376), herpes simplex virus (Boursnell et al, 1998, *Adv. Exp. Med. Biol.* 451:379-84), HIV, adeno-associated viruses (AAV), vaccinia or parvovirus may be utilised to deliver a nucleic acid molecule to target cells.

Alternatively, non-viral methods may be used to deliver nucleic acid molecules to target cells (Ledley, 1995, *Human Gene Therapy* 6, 1129-1144). For example, "naked" nucleic acid or nucleic acid molecules complexed with cationic and neutral lipids may be injected or perfused directly into the synovium. Conveniently, nucleic acid molecules may be administered via a hydrogel material, which is non-inflammatory and biodegradable (for example, PluronicR-based hydrogels available from BASF Corp., Parsippany, N.J., USA).

Additionally, the nucleic acid molecule may be administered by means of implants that are commercially available or described in the scientific literature, such as liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the nucleic acid molecules.

Other suitable methods involve the delivery of the nucleic acid molecule into the target cell using liposomes (see Nassander et al (1992) *Cancer Res.* 52, 646-653). For example, immunoliposomes (ie. antibody-directed liposomes) are especially useful in targeting specific populations of cells, such as synovial cells.

A second aspect of the present invention provides a method of identifying a compound with efficacy in the treatment of a chronic inflammatory disease comprising the step of testing said compound for an ability to selectively inhibit $T_{ck}$ cells.

It will be appreciated by persons skilled in the art that such a compound may be a drug-like compound or lead compound for the development of a drug-like compound.

The term "drug-like compound" is well known to those skilled in the art, and includes a compound having characteristics that may make it suitable for use in medicine, for example as the active ingredient in a medicament. Thus, for example, a drug-like compound may be a molecule that may be synthesised by the techniques of organic chemistry, molecular biology or biochemistry, and is preferably a small molecule, which may be of less than 5000 daltons and which may be water-soluble. A drug-like compound may additionally exhibit features of selective interaction with a particular protein or proteins and be bioavailable and/or able to penetrate target cellular membranes, but it will be appreciated that these features are not essential.

The term "lead compound" is similarly well known to those skilled in the art, and may include a compound which, whilst not itself suitable for use as a drug (for example because it is only weakly potent against its intended target, non-selective in its action, unstable, poorly soluble, difficult to synthesise or has poor bioavailability), may provide a starting-point for the design of other compounds that may have more desirable characteristics.

By "efficacy in the treatment of a chronic inflammatory disease" we include efficacy in the therapeutic and/or prophylactic treatment of a chronic inflammatory disease, for example an ability to prevent the onset and/or progression of said disease, and/or to alleviate the symptoms of said disease.

It will be appreciated by persons skilled in the art that functional inhibition of $T_{ck}$ cells includes inhibition of the interaction of $T_{ck}$ cells with monocytes/macrophages, for example the direct cell-cell interaction between $T_{ck}$ cells and monocytes/macrophages that induces the production of pro-inflammatory cytokines by monocytes/macrophages.

In a preferred embodiment of the second aspect of the invention, the method comprises testing said compound for an ability to selectively inhibit $T_{ck}$ cell-induced release of one or more pro-inflammatory cytokines from monocytes/macrophages.

Advantageously, the one or more pro-inflammatory cytokines is or includes tumour necrosis factor α (TNFα). Conveniently, the one or more pro-inflammatory cytokines is or includes IL-15.

By "a chronic inflammatory disease" we include any disease in which there is a progressive and sustained anti-self (i.e. autoimmune) response, typically leading to the development of tissue inflammation and, in severe cases, destruction of said tissue.

Preferably, the chronic inflammatory disease is a disease of humans. Such diseases include, but are not limited to, rheumatoid arthritis, Crohn's disease, multiple sclerosis and atherosclerosis. In principle, the invention is applicable to other mammals and birds, including pets such as dogs and cats and agriculturally important animals such as cows, horses, sheep, pigs, chickens and turkeys.

Advantageously, the chronic inflammatory disease is rheumatoid arthritis.

It will be understood that it is desirable to identify compounds that may modulate the function of $T_{ck}$ cells in vivo. Thus, it will be understood that reagents and conditions used in the methods of the invention may be chosen such that the interactions between said compounds and $T_{ck}$ cells are substantially the same as would occur in vivo.

In principle, one may use any test for inhibition of T cells, and one determines whether the inhibition is greater in the case of $T_{ck}$ cells than other T cells, especially $T_{tcr}$ cells.

In a preferred embodiment of the second aspect of the present invention, testing the compound for an ability to selectively inhibit $T_{ck}$ cell-induced release of one or more pro-inflammatory cytokines from monocytes comprises the following steps:

(i) pre-incubating monocytes with a compound to be tested;

(ii) resuspending said pre-incubated monocytes in the absence of the test compound;

(iii) stimulating said resuspended monocytes by co-culturing with either $T_{ck}$ cells or $T_{tcr}$ cells; and (iv) assaying for TNFα production by said stimulated monocytes.

Preferably, step (i) comprises preparing monocytes from single donor plateletpheresis residues (e.g. purchased from the North London Blood Transfusion Service, Colindale, UK) as follows; mononuclear cells are isolated by Ficoll/Hypaque centrifugation (specific density 1.077 g/ml, Nycomed Pharma A. S., Oslo, Norway), prior to monocyte separation in a Beclanan JE6 elutriator. Elutriation is then performed in culture medium containing 1% heat inactivated FCS. The monocytes are then cultured at $1 \times 10^6$ cells/ml in RPMI 1640 (containing 5% heat inactivated FCS) in triplicate in round-bottomed 96-well plates (Nunc Life Technologies Ltd, Paisley, Scotland) for 15 minutes at 37° C. in the presence of the compound to be tested. Typically, the compound to be tested is included in the culture medium at a concentration range of 0 to 100 μM. Following pre-incubation, cell viability may be determined, for example using the MTT assay (3-(4,5-dimethylthiazol-2-yl)-2,5-diphenyltetrazolium bromide).

Cell viability of greater than 90% is considered acceptable. If viability is less than 90%, step (i) may be repeated.

Conveniently, steps (ii) and (iii) occur simultaneously, immediately after the pre-incubation period of step (i) is complete.

Preferably, step (iii) comprises co-culturing the pre-incubated monocytes in RPMI 1640 (containing 5% heat inactivated FCS) in triplicate in round-bottomed 96-well plates for 18 hours at 37° C. with $T_{tcr}$ cells or $T_{ck}$ cells at different ratios (e.g. 1:1, 3:1, 5:1, 7:1 T cells to monocytes). Efficient fixation of T cells may be tested by incubating an aliquot of T cells ($7 \times 10^6$ cells/ml) in the absence of monocytes and assaying the amount of TNFα released by the cells under these conditions. Lipopolysaccharide (LPS, 5 ng/ml) may be included in experiments as a positive control for monocyte cytokine production. At the end of the co-culture period, cell suspensions may again be assayed for cell viability using the MTT assay.

Preferably, step (iv) comprises harvesting the culture supernatants and assaying for TNFα production by ELISA (see Examples). Supernatant samples may be stored at −20° C. prior to assaying for TNFα production.

In an alternative embodiment of the second aspect of the invention, wherein compounds are tested for a direct inhibitory effect on $T_{ck}$ cells, the method comprises the following steps:

(i) pre-incubating separate cultures of $T_{ck}$ cells and $T_{tcr}$ cells with a compound to be tested either prior to fixation, or during their activation in culture (by cytokine cocktail or anti-CD3 antibodies, respectively);

(ii) resuspending said $T_{ck}$ cells and $T_{tcr}$ cells in the absence of the test compound;

(iii) stimulating monocytes by co-culturing with said resuspended fixed $T_{ck}$ cells or $T_{tcr}$ cells; and (iv) assaying for TNFα production by said stimulated monocytes.

Preferably, step (iii) comprises co-culturing monocytes in RPMI 1640 (containing 5% heat inactivated FCS) in triplicate in round-bottomed 96-well plates for 18 hours at 37° C. with fixed $T_{tcr}$ cells or $T_{ck}$ cells at different ratios (e.g. 1:1, 3:1, 5:1, 7:1 T cells to monocytes). Efficient fixation of T cells may be tested by incubating an aliquot of T cells ($7 \times 10^6$ cells/ml) in the absence of monocytes and assaying the amount of TNFα released by the cells under these conditions. Lipopolysaccharide (LPS, 5 ng/ml) may be included in experiments as a positive control for monocyte cytokine production. At the end of the co-culture period, cell suspensions may again be assayed for cell viability using the MTT assay.

Preferably, step (iv) comprises harvesting the culture supernatants and assaying for TNFα production by ELISA (see Examples). Supernatant samples may be stored at −20° C. prior to assaying for TNFα production.

Inhibition of $T_{ck}$ cells is deemed to occur if $T_{ck}$ cell-stimulated release of pro-inflammatory cytokines (e.g. TNFα) by monocytes is reduced to no more than 50% compared to pro-inflammatory cytokine production by monocytes stimulated with $T_{ck}$ cells which are not pre-incubated with the test compound. Preferably, $T_{ck}$ cell-stimulated release of pro-inflammatory cytokines (e.g. TNFα) by monocytes is reduced to no more than 20%, 10%, 5% or 1%.

Selective compounds of the present invention include those compounds which selectively inhibit pro-inflammatory cytokine (e.g. TNFα) production by monocytes/macrophages stimulated with $T_{ck}$ cells to a greater extent than they inhibit pro-inflammatory cytokine production by monocytes/macrophages stimulated with $T_{tcr}$ cells. The inhibition of $T_{ck}$ cells (i.e. the inhibition of $T_{ck}$ cell-induced release of one or more pro-inflammatory cytokines from monocytes) is deemed to be selective if the inhibitory effect of the compound on $T_{ck}$ cell-induced release of one or more pro-inflammatory cytokines from monocytes is at least two-fold greater than the effect of the compound on $T_{tcr}$ cell-induced release of one or more pro-inflammatory cytokines from monocytes. Preferably, the effect of the compound on $T_{ck}$ cell-induced release of pro-inflammatory cytokines from monocytes is at least three-fold, five-fold or ten-fold greater than the effect of the compound on $T_{tcr}$ cell-induced release of pro-inflammatory cytokines from monocytes.

Ideally, $T_{ck}$ cell-stimulated release of pro-inflammatory cytokines by monocytes is substantially zero while pro-inflammatory cytokine production by monocytes stimulated with $T_{tcr}$ cells is substantially unaffected.

In a further preferred embodiment of the second aspect of the present invention, testing the compound for an ability to selectively inhibit $T_{ck}$ cells or selectively inhibit $T_{ck}$ cell-induced release of one or more pro-inflammatory cytokines from monocytes comprises assaying for NF-κB inhibition in monocytes.

By "NF-κB inhibition" we include one or more of the following:

(i) a reduction in expression of NF-κB-dependent genes;

(ii) a reduction in the ability for NF-κB to bind to its promoter on DNA;

(iii) a decrease in translation of NF-κB; and/or (iv) a decrease in transcription of NF-κB.

Conveniently, NF-κB inhibition is deemed to exist if, when monocytes are incubated in culture with a compound, and nuclear extracts are prepared from the monocytes, the nuclear extracts exhibit a reduced binding to the NF-κB promoter on DNA oligonucleotides. The latter can be shown using an electrophoretic mobility shift assay (EMSA). Preferably, the binding is reduced to no more than 50% compared to the binding of nuclear extracts prepared from monocytes that have not been pre-incubated with the test compound, preferably no more than 20%, 10%, 5% or 1%. Ideally, the binding is substantially zero.

An exemplary EMSA is described in Clarke et al. (1995) *Eur. J. Immunol.* 25:2961-2966.

Advantageously, NF-κB inhibition is deemed to exist if, in a reporter gene assay wherein the NF-κB gene (or at least the promoter thereof) is coupled to a β-galactosidase gene in a cell line, β-galactosidase activity in the cell lysates is reduced following incubation of the cells with a test compound. Preferably, β-galactosidase activity is reduced to no more than 50% compared to β-galactosidase activity in lysates from cells which have not been incubated with the test compound, and more preferably to no more than 20%, 10%, 5% or 1%. Ideally, β-galactosidase activity is substantially zero.

An exemplary reporter gene assay is described in Clarke et al. (1995) *Eur. J. Immunol.* 25:2961-2966.

In an alternative preferred embodiment of the methods of identifying a compound of the present invention, testing the compound for an ability to selectively inhibit $T_{ck}$ cells or to selectively inhibit $T_{ck}$ cell-induced release of one or more pro-inflammatory cytokines from monocytes comprises assaying for PI3 kinase activation in monocytes.

Conveniently, PI3 kinase activation is deemed to exist if, when monocytes are incubated in culture with a compound, PI3 kinase activity is increased. This may be determined by lysing the monocytes, harvesting the supernatant, immunoprecipitating PI3 kinase from the supernatant, and assaying the immunoprecipitate for PI3 kinase activity (Hayes et al, 1999, *J. Biol. Chem.* 274:33455-33461).

The monocytes in such a case may be human peripheral blood monocytes or a monocyte cell line, such as Mono Mac-6 (Zeigler-Heitbrock et al, *Int. J. Cancer* 1988, 41, 456-461).

It will be appreciated that screening assays which are capable of high throughput operation will be particularly preferred. Examples may include cell-based assays and protein-protein binding assays. A SPA-based (Scintillation Proximity Assay; Amersham International) system may be used. For example, an assay for identifying a compound capable of modulating the activity of a protein kinase may be performed as follows. Beads comprising scintillant and a polypeptide that may be phosphorylated may be prepared. The beads may be mixed with a sample comprising the protein kinase and $^{32}$P-ATP or $^{33}$P-ATP, together with the test compound. Conveniently this is done in a 96-well format. The plate is then counted using a suitable scintillation counter, using known parameters for $^{32}$P or $^{33}$P SPA assays. Only $^{32}$P or $^{33}$P that is in proximity to the scintillant, i.e. only the radioisotope bound to the polypeptide, is detected. Variants of such an assay, for example in which the polypeptide is immobilised on the scintillant beads via binding to an antibody, may also be used.

A further method of identifying a compound that is capable of binding to the polypeptide (such as NF-κB or PI3 kinase) comprises exposing the polypeptide to a test compound and measuring any binding of said compound to the said polypeptide. The binding constant for the binding of the compound to the polypeptide may be determined. Suitable methods for detecting and/or measuring (quantifying) the binding of a compound to a polypeptide are well known to those skilled in the art and may be performed, for example, using a method capable of high throughput operation, for example a chip-based method. New technology, called VLSIPS™, has enabled the production of extremely small chips that contain hundreds of thousands or more of different molecular probes. These biological chips or arrays have probes arranged in arrays, each probe assigned a specific location. Biological chips have been produced in which each location has a scale of, for example, 10 µm. The chips can be used to determine whether target molecules interact with any of the probes on the chip. After exposing the array to target molecules under selected test conditions, scanning devices can examine each location in the array and determine whether a target molecule has interacted with the probe at that location.

Biological chips or arrays are useful in a variety of screening techniques for obtaining information about either the probes or the target molecules. For example, a library of peptides can be used as probes to screen for drugs. The peptides can be exposed to a receptor, and those probes that bind to the receptor can be identified (for example, see U.S. Pat. No. 5,874,219 issued 23 Feb. 1999 to Rava et al).

According to a third aspect of the present invention, there is provided a compound identifiable or identified by a method according to the second aspect of the invention, for use in the treatment of a chronic inflammatory disease. Such compounds include tyloxapol (Ghio et al, *Am J Respir Crit. Care Med* 1996, 154, 783-8), panepoxydone (Erkel et al, *Biochem Biophys Res Commun* 1996, 226, 214-21), emodin (Kumar et al, *Oncogene* 1998, 17, 913-9138), anetholdithiolthione (Sen et al, *Biochem Biophys Res Commun* 1996, 218, 148-53), retinoids (Na et al, *J Biol Chem* 1999, 274, 7674-80), phenylalanine chloromethyl ketone (PCK) (Jeong et al, *Immunology* 1997, 92, 267-73), sanguinarine (Chaturvedi et al, *J Biol Chem* 1997, 272, 30129-34), $\Delta^9$-tetrahydrocannabinol (Jeon et al, *Mol Pharmacol* 1996, 50, 334-341), gliotoxin, sesquiterpene lactones (Hehnert et al, *J Biol Chem* 1998, 272, 1288-97; Lyss et al, *J Biol Chem* 1998, 273, 33508-16), caffeic acid phenethyl ester (Natarajau et al, *Proc. Nat. Acad. Sci. USA*, 1996, 93, 9090-5), pyrrolidine dithiocarbamate (Schreck et al, *J Exp Med* 1992; 175: 1181-94), lovastatin (Merck), azelastine HCl (Azeptin, Eisai Co. Tokyo), tepoxalin (Kazmi et al, *J Cell Biochem* 1995; 57: 299-310), epigallocatechin-3-gallate (Lin & Lin, *Mol Pharmacol* 1997; 52: 465-72), deoxyspergualin (Bristol-Myers Squibb), phenyl-N-tert-butylnitrone (Aldrich Chemical Co), quercetin (Sato et al, *J Rheumatol* 1997; 24: 1680 4), curcumin, E3330 (a quinone derivative Tsukuba Research Labs, Eisai Co. Japan), and proteasome inhibitors, such as PSI (Calbiochem), ALLN (Boehringer Mannheim), lactacystin (Delic et al, *Br. J. Cancer* 1998; 77: 1130-7), MG-132 (Peptide International), X-LFF and the Calpain inhibitors reviewed by Beauparlant & Hiscott, *Cytokine & Growth Factor Reviews* 1996; 7: 175-90, and CVT-634 (CV Therapeutics, Palo Alto).

It will be appreciated that any compound according to the third aspect of the invention should be sufficiently non-toxic to allow use of the compound at a therapeutic dose.

In a preferred embodiment of the third aspect of the present invention, the compound selectively inhibits $T_{ck}$ cell-induced release of one or more pro-inflammatory cytokines from monocytes. Conveniently, release of said cytokines is assayed by enzyme-linked immunosorbent assay (ELISA), for example as described in Sebbag et al (1997) *Eur. J. Immunol.* 27:624-632.

Advantageously, the one or more pro-inflammatory cytokine is or includes TNFα.

It will be appreciated that the compounds of the invention may decrease the activity of NF-κB, e.g. by binding substantially reversibly or substantially irreversibly to the active site of the NF-κB polypeptide. In a further example, the compound may bind to a portion of said polypeptide that is not the active site so as to interfere with the binding of the said polypeptide to its substrate. In a still further example, the compound may bind to a portion of said polypeptide so as to decrease said polypeptide's activity by an allosteric effect. This allosteric effect may be an allosteric effect that is involved in the natural regulation of the said polypeptide's activity, for example in the activation of said polypeptide by an "upstream activator".

It will also be understood that the compounds of the invention may decrease the activity of NF-κB by binding to one or more of the subunits of NF-κB, namely p65(RelA), RelB, cREL, p50, p52, p105 (precursor to p50) and p100 (precursor to p52).

In a further embodiment of the third aspect of the invention, the compound increases the activity of PI3 kinase, e.g. by binding substantially reversibly or substantially irreversibly to the active site of the of PI3 kinase polypeptide. Alternatively, the compound may bind to a portion of this polypeptide that is not the active site so as to aid the binding of the said polypeptide to its substrate. In a still further example, the compound may bind to a portion of said polypeptide so as to increase said polypeptide's activity by an allosteric effect. This allosteric effect may be an allosteric effect that is involved in the natural regulation of the said polypeptide's activity for example in the activation of the said polypeptide by an "upstream activator".

A fourth aspect of the invention provides an antibody-like molecule having specificity for $T_{ck}$ cells.

By "antibody-like molecule" we include whole antibodies (e.g. monoclonal or polyclonal antibodies) having specificity for $T_{ck}$ cells and fragments of such antibodies which retain a specificity for $T_{ck}$ cells. Preferably, the antibody-like molecule is a monoclonal antibody or antigen-binding fragment thereof.

By "having specificity for $T_{ck}$ cells" we mean that the antibody-like molecule is capable of binding $T_{ck}$ cells via the antigen-recognition site of said monoclonal antibody or fragment thereof. For example, the antibody-like molecule may have affinity for an antigen expressed on the surface of $T_{ck}$ cells.

Preferably, the antibody-like molecule recognises $T_{ck}$ cells with high avidity.

By "high avidity" we mean that the antibody-like molecule binds to the $T_{ck}$ cells with a binding constant (Kd) of at least $10^{-6}$ M, preferably at least $10^{-9}$ M, suitably $10^{-10}$ M, more suitably $10^{-11}$ M, yet more suitably $10^{-12}$ M, and most preferably $10^{-15}$ M or even $10^{-18}$ M.

Advantageously, the antibody-like molecule has selective specificity for $T_{ck}$ cells, i.e. it binds to $T_{ck}$ cells but does not bind substantially to other populations of T cell, such as $T_{tcr}$ cells.

Antigen-binding specificity is determined by variable heavy (VH) and variable light (VL) domains of the antibody, a fact first recognised by early protease digestion experiments. For example, it has been shown that variable domains of rodent origin may be fused to constant domains of human origin such that the resultant antibody retains the antigenic specificity of the rodent parent antibody (Morrison et al (1984) *Proc. Natl. Acad. Sci. USA* 81, 6851-6855).

A preferred embodiment of the fourth aspect of the invention provides an antigen-binding fragment of an antibody with specificity for $T_{ck}$ cells. Such antibody-like molecules and the clinical use thereof are reviewed in Hudson (1998) *Curr. Opin. Biotechnol.* 9(4), 395-402 and Holliger & Bohlen (1999) *Cancer Metastasis Rev.* 18(4), 411-9.

Suitable antigen-binding fragments include Fab-like molecules (Better et al (1988) *Science* 240, 1041); Fv molecules (Skerra et al (1988) *Science* 240, 1038); disulphide-linked Fv molecules (Young et al., 1995, *FEBS Lett.* 377:135-139); single-chain Fv (ScFv) molecules where the VH and VL partner domains are linked via a flexible oligopeptide (Bird et al (1988) *Science* 242, 423; Huston et al (1988) *Proc. Natl. Acad. Sci. USA* 85, 5879) and single domain antibodies (dabs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

The advantages of using antibody fragments, rather than whole antibodies, are several-fold. For example, Fab, Fv, ScFv, disulphide Fv and dAb antibody fragments can all be expressed recombinantly in bacteria, such as *E. coli*, or eukaryotic expression systems such as yeast or mammalian systems, thus allowing the facile production of large amounts of the said fragments. In addition, the smaller size of the fragments allows for rapid clearance from the body in clinical applications.

In a further preferred embodiment of the fourth aspect of the invention, the antibody-like molecule is humanised.

By 'humanised monoclonal antibody' we include monoclonal antibodies having at least one chain wherein the framework regions are predominantly derived from a first, acceptor monoclonal antibody of human origin and at least one complementarity-determining region (CDR) is derived from a second, donor monoclonal antibody having specificity for $T_{ck}$ cells. The donor monoclonal antibody may be of human or non-human origin, for example it may be a murine monoclonal antibody.

Preferably, both chains of the humanised monoclonal antibody comprise CDRs grafted from a donor monoclonal antibody having specificity for $T_{ck}$ cells.

Advantageously, the CDR-grafted (i.e. humanised) chain comprises two or all three CDRs derived from a donor antibody having specificity for $T_{ck}$ cells.

Conveniently, the humanised monoclonal antibody comprises only human framework residues and CDRs from a donor antibody having specificity for $T_{ck}$ cells.

However, it will be appreciated by those skilled in the art that in order to maintain and optimise the specificity of the humanised antibody it may be necessary to alter one or more residues in the framework regions such that they correspond to equivalent residues in the donor antibody.

Conveniently, the framework regions of the humanised antibody are derived from a human IgG monoclonal antibody.

Methods of making humanised monoclonal antibodies are well-known in the art, for example see Jones et al (1986) *Nature* 321:522-525, Riechmann et al (1988) *Nature* 332: 323-327, Verhoeyen et al (1988) *Science* 239:1534-1536 and EP 239 400 (to Winter).

It will be understood by persons skilled in the art that where the patient is not human, for example where the patient is a dog or horse, the CDR regions of non-human antibodies of desired specificity are inserted into the framework regions of an appropriate non-human antibody, e.g. a dog or horse antibody, respectively.

Having designed or selected an antibody-like molecule having the desired specificity, the antibody may be made using recombinant DNA techniques.

A fifth aspect of the invention provides a method of making an antibody-like molecule according to the fourth aspect of the invention comprising immunising an animal with a population of $T_{ck}$ cells.

It will be appreciated by persons skilled in the art that the animal may be immunised with whole $T_{ck}$ cells or membrane preparations from such cells. Suitable membrane preparations may be prepared using techniques well known in the art, for example by lysing the cells and isolating the membranes by sucrose density gradient separation.

Preferably, the animal is selected from the group consisting of mouse, rabbit and sheep.

Methods of making suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982) and "*Antibody Engineering, A Practical Approach*", McCafferty, J. et al, ed. (IRL Press, 1996).

In a preferred embodiment, the method comprises the following steps:

(i) injecting 3 to 4 month old mice intra-peritoneally (i.p.) with $10^7$ $T_{ck}$ cells (in phosphate buffered saline) on days 0, 14 and 21;

(ii) removing a sample of blood from the mice on day 28 and testing for the presence of anti-$T_{ck}$ cell antibodies in said sample;

(iii) injecting mice found to have high levels of anti-$T_{ck}$ cell antibodies intravenously (i.v.) with $10^7$ $T_{ck}$ cells (in phosphate buffered saline) on day 35;

(iv) harvesting the spleen from the mice on day 38 and fusing the B-lymphocytes therefrom with an immortalised cell line to generate hybridomas; and (v) screening said immortalised cell fusions of step (iv) to determine whether they express an antibody having specificity for $T_{ck}$ cells Preferably, testing for the presence of anti-$T_{ck}$ cell antibodies in said sample in step (ii) comprises by flow cytometry using $T_{ck}$ cells as target antigen, and resting T cells as controls.

Conveniently, step (v) is performed by flow cytometry screening against $T_{ck}$ cells as a positive target and against $T_{tcr}$ cells as a negative target.

When mice are immunised with human cells, a strong response against species antigens is evoked. In the above method, the generation of $T_{ck}$ cell selective antibodies may be optimised by pre-coating the $T_{ck}$ cells prior to injection with mouse antibodies specific for other human cell populations, e.g. mouse anti-$T_{tcr}$ cell antibodies. This pre-coating step 'hides' immunogenic surface proteins commonly found on human cell types other than $T_{ck}$ cells.

Thus, a sixth aspect of the invention provides an isolated cell, such as a hybridoma cell, which expresses an antibody having specificity for $T_{ck}$ cells.

A seventh aspect of the invention provides a method for identifying a antibody-like molecule according to the fourth aspect of the invention comprising the following steps:

(i) providing a population of $T_{ck}$ cells; and (ii) using said $T_{ck}$ cells to screen a library of antibody-like molecules.

In a preferred embodiment, a membrane preparation is made from the $T_{ck}$ cells which is then used to screen the antibody-like molecule library. Suitable membrane preparations may be made using techniques well known in the art, for example by lysing the $T_{ck}$ cells and separating the membrane fraction by sucrose gradient centrifugation.

Preferably, the antibody-like molecule library is a phage display library.

Advantageously, step (ii) comprises screening the phage display library by sequential negative and positive panning against fixed or non-fixed $T_{tcr}$ (negative) and $T_{ck}$ (positive) cells.

The display of proteins and polypeptides on the surface of bacteriophage (phage), fused to one of the phage coat proteins, provides a powerful tool for the selection of specific ligands. This 'phage display' technique was originally used by Smith in 1985 (*Science* 228, 1315-7) to create large libraries of antibodies for the purpose of selecting those with high affinity for a particular antigen. More recently, the method has been employed to present peptides, domains of proteins and intact proteins at the surface of phages in order to identify ligands having desired properties.

The principles behind phage display technology are as follows:

(i) Nucleic acid encoding the protein or polypeptide for display is cloned into a phage;

(ii) The cloned nucleic acid is expressed fused to the coat-anchoring part of one of the phage coat proteins (typically the p3 or p8 coat proteins in the case of filamentous phage), such that the foreign protein or polypeptide is displayed on the surface of the phage; and (iii) The phage displaying the protein or polypeptide with the desired properties is then selected (e.g. by affinity chromatography) thereby providing a genotype (linked to a phenotype) that can be sequenced, multiplied and transferred to other expression systems.

Alternatively, the foreign protein or polypeptide may be expressed using a phagemid vector (ie. a vector comprising origins of replication derived from a phage and a plasmid) that can be packaged as a single stranded nucleic acid in a bacteriophage coat. When phagemid vectors are employed, a "helper phage" is used to supply the functions of replication and packaging of the phagemid nucleic acid. The resulting phage will express both the wild type coat protein (encoded by the helper phage) and the modified coat protein (encoded by the phagemid), whereas only the modified coat protein is expressed when a phage vector is used.

Methods of selecting phage expressing a protein or peptide with a desired specificity are known in the art. For example, a widely used method is "panning", in which phage stocks displaying ligands are exposed to solid phase coupled target molecules, e.g. using affinity chromatography.

Alternative methods of selecting phage of interest include SAP (Selection and Amplification of Phages; as described in WO 95/16027) and SIP (Selectively-Infective Phage; EP 614989A, WO 99/07842), which employ selection based on the amplification of phages in which the displayed ligand specifically binds to a ligand binder. In one embodiment of the SAP method, this is achieved by using non-infectious phage and connecting the ligand binder of interest to the N-terminal part of p3. Thus, if the ligand binder specifically binds to the displayed ligand, the otherwise non-infective ligand-expressing phage is provided with the parts of p3 needed for infection. Since this interaction is reversible, selection can then be based on kinetic parameters (see Duenas et al., 1996, *Mol. Immunol.* 33, 279-285).

The use of phage display to isolate ligands that bind biologically relevant molecules has been reviewed in Felici et al (1995) *Biotechnol. Annual Rev.* 1, 149-183, Katz (1997) *Annual Rev. Biophys. Biomol. Struct.* 26, 27-45 and Hoogenboom et al (1998) *Immunotechnology* 4(1), 1-20. Several randomised combinatorial peptide libraries have been constructed to select for polypeptides that bind different targets, e.g. cell surface receptors or DNA (reviewed by Kay, 1995, Perspect. Drug Discovery Des. 2, 251-268; Kay and Paul, 1996, Mol. Divers. 1, 139-140). Proteins and multimeric proteins have been successfully phage-displayed as Functional molecules (see EP 0349578A, EP 0527839A, EP 0589877A; Chiswell and McCafferty, 1992, *Trends Biotechnol.* 10, 80-84). In addition, functional antibody fragments (e.g. Fab, single chain Fv [scFv]) have been expressed (McCafferty et al., 1990, *Nature* 348, 552-554; Barbas et al., 1991, *Proc. Natl. Acad. Sci. USA* 88, 7978-7982; Clackson et al., 1991, *Nature* 352, 624-628), and some of the shortcomings of human monoclonal antibody technology have been superseded since human high affinity antibody fragments have been isolated (Marks et al., 1991, *J. Mol. Biol.* 222, 581-597; Hoogenboom and Winter, 1992, *J. Mol. Biol.* 227, 381-388). Further information on the principles and practice of phage display is provided in *"Phage display of peptides and proteins: a laboratory manual"* Ed Kay, Winter and McCafferty (1996) Academic Press, Inc ISBN 0-12-402380-0.

Examples of the identification of target cell specific antibodies using phage display technology are described in de Kruif et al (1995) *Proc. Natl. Acad. Sci. USA* 92: 3938-42, Cai and Green, 1995, *Proc. Natl. Acad. Sci. USA* 92: 6537-41. Detailed method for the phage selection of antibody fragments on whole cells are disclosed in Coligan et al (eds.) "Current Protocols in Immunology", Vol 3, Wiley Press, New York, pages 17.1.25 to 17.1.26.

An eighth aspect of the invention provides a compound comprising a target cell specific portion and a directly or indirectly cytotoxic portion, wherein the target cell specific portion comprises an antibody-like molecule according to fourth aspect of the invention.

By "directly or indirectly cytotoxic", we include the meaning that the moiety may itself be toxic (for example radionuclides, ricin, ribonuclease, deoxyribonuclease, and *Pseudomonas* exotoxin A) or it may be metabolised to form a toxic product, or it may act on something else to form a toxic product.

In relation to the indirectly cytotoxic portion, the moiety may be an enzyme capable of converting a substantially non-toxic prodrug to a toxic drug. Examples of such enzyme/prodrug systems include, but are not limited to (i) cytosine deaminase, e.g. from *E. coli* or *S. cerevisiae*), which converts 5-fluorocytosine (5FC) to 5-fluorouracil (5FU) (Mullen et al, 1922, *Proc. Natl. Acad. Sci. USA* 89, 33);

(ii) the herpes simplex enzyme thymidine kinase, which sensitises cells to treatment with the antiviral agent ganciclovir (GCV) or aciclovir (Moolten, 1986, *Cancer Res.* 46, 5276; Ezzedine et al, 1991, *New Biol* 3, 608);

(iii) alkylating agents, e.g. a benzoic acid mustard released from para-N-bis(2-chloroethyl)aminobenzoyl glutamic acid by the action of *Pseudomonas* sp. CPG2 enzyme;

(iv) cyanogenic monosaccharides or disaccharides, such as the plant compound amygdalin, which release cyanide upon the action of a β-glucosidase and hydroxynitrile lyase (WO 91/11201); and (v) alkaline phosphatases in conjunction with the pro-drug etoposide 4'-phosphate or 7-(2'-aminoethyl phosphate)mitomycin or a combination thereof have been disclosed (EP 0 302 473; Senter et al (1988) *Proc. Natl. Acad. Sci. USA* 85, 4842).

Conveniently, the cytotoxic portion is an enzyme.

In a preferred embodiment, the cytotoxic portion is capable of inducing apoptosis, or 'programmed cell death', of the target cells.

Exemplary cytotoxic portions capable of inducing apoptosis of the target cells (i.e. $T_{ck}$ cells) include the TNF receptor-associated death domain (TRADD) and the Fas-associated death domain (FADD) (see Schneider and Tschopp, 2000, *J. Pharm. Acta. Helv.* 74:281-6).

In a preferred embodiment of the compound according to eighth aspect of the invention, the target cell specific portion and the cytotoxic portion are fused. Thus, there is provided a fusion protein comprising a target cell specific portion and the cytotoxic portion.

By "fusion compound" we include a compound comprising one or more functionally distinct portions, wherein the distinct portions are contained within a single polypeptide chain produced by recombinant DNA techniques.

Preferably, the target-cell specific portion and the cytotoxic portion of the fusion compound of the invention are separated by a linker sequence, for example to allow greater flexibility of the portions relative to one another.

Alternatively, the target-cell specific portion and the cytotoxic portion of the compound of the invention are separate moieties linked together by any of the conventional ways of cross-linking polypeptides, such as those generally described in O'Sullivan et al *Anal. Biochem.* (1979) 100, 100-108. For example, the antibody portion may be enriched with thiol groups and the enzyme portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

A ninth aspect of the invention provides an isolated nucleic acid molecule encoding a fusion protein compound according to the eighth aspect of the invention, or a target cell-specific portion or cytotoxic portion thereof.

By "nucleic acid molecule" we include DNA, cDNA and mRNA molecules.

A tenth aspect of the present invention provides a method of making a compound according to the eighth aspect of the invention, said method comprising expressing one or more nucleic acid molecules according to the ninth aspect of the invention in a host cell and isolating the compound therefrom.

It is preferable that the two portions of the compound of the invention are produced as a fusion compound by recombinant DNA techniques, whereby a length of DNA comprises respective regions encoding the two portions of the compound of the invention either adjacent one another or separated by a region encoding a linker peptide which does not destroy the desired properties of the compound. The DNA is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859 issued 3 Apr. 1984 to Rutter et al, 4,530,901 issued 23 Jul. 1985 to Weissman, 4,582,800 issued 15 Apr. 1986 to Crowl, 4,677,063 issued 30 Jun. 1987 to Mark et al, 4,678,751 issued 7 Jul. 1987 to Goeddel, 4,704,362 issued 3 Nov. 1987 to Itakura et al, 4,710,463 issued 1 Dec. 1987 to Murray, 4,757, 006 issued 12 Jul. 1988 to Toole, Jr. et al, 4,766,075 issued 23 Aug. 1988 to Goeddel et al and 4,810,648 issued 7 Mar. 1989 to Stalker.

The DNA encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae* and *Pichia pastoris*), filamentous fungi (for example *Aspergillus*), plant cells, animal cells (for example COS-1, COS-7, CHO, NIH 3T3, NS0 and BHK cells) and insect cells (for example *Drosophila*, SF9 cells).

Those vectors that include a replicon such as a procaryotic replicon can also include an appropriate promoter such as a procaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical procaryotic vector plasmids are pUC18, pUC19, pBR322 and pBR329 (available from Biorad Laboratories, Richmond, Calif., USA), pTrc99A and pKK223-3 (available from Pharmacia Piscataway, N.J., USA) and the pET system (T7 promoter, Novagen Ltd).

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers his 3, trp1, leu2 and ura3. Plasmids pRS413-416 are Yeast Centromere plasmids (YCps).

Further useful vectors for transformation of yeast cells, such as *Pichia*, include the 2μ plasmid pYX243 (available from R and D Systems Limited) and the integrating vector pPICZ series (available from Invitrogen).

A variety of methods have been developed to operatively link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide constituting the compound of the invention is to use the polymerase chain reaction as disclosed by Saiki et al (1988) *Science* 239, 487-491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

The present invention also relates to a host cell transformed with a polynucleotide vector construct of the present invention. The host cell can be either procaryotic or eukaryotic. Bacterial cells are preferred procaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast and mammalian cells, preferably vertebrate cells such as those from a mouse, rat, monkey or human fibroblastic cell line. Preferred eukaryotic host cells include Chinese hamster ovary (CHO) cells available from the ATCC as CCL61, NIH Swiss mouse embryo cells NIH/3T3 available from the ATCC as CRL 1658 and monkey kidney-derived COS-1 cells available from the ATCC as CRL 1650 or WSO cells.

Transformation of appropriate cell hosts with a DNA construct of the present invention is accomplished by well known methods that typically depend on the type of vector used. With regard to transformation of procaryotic host cells, see, for example, Cohen et al, 1972, *Proc. Natl. Acad. Sci. USA*, 69: 2110 and Sambrook et al, *Molecular Cloning, A Laboratory Manual*, Cold Spring Harbor Laboratory, Cold Spring Harbor, N.Y. (1989). Transformation of yeast cells is described in Sherman et al, *Methods In Yeast Genetics, A Laboratory Manual*, Cold Spring Harbor, N.Y. (1986). The method of Beggs, *Nature*, 275: 104-109 (1978) is also useful. With regard to vertebrate cells, reagents useful in transfecting such cells, for example calcium phosphate and DEAE-dextran or liposome formulations, are available from Stratagene Cloning Systems, or Life Technologies Inc, Gaithersburg, Md. 20877, USA.

Successfully transformed cells, i.e. cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern, 1975, *J. Mol. Biol.*, 98: 503 or Berent et al, 1985, *Biotech.*, 3: 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains the protein.

Nutrient media useful for culturing transformed host cells are well known in the art and can be obtained from several commercial sources.

A eleventh aspect of the invention provides a vector for expression of a fusion protein compound according to the eighth aspect of the invention, or a target cell-specific portion or cytotoxic portion thereof, said vector comprising a nucleic acid molecule according to the ninth aspect of the invention.

A twelfth aspect of the invention provides a host cell comprising a nucleic acid molecule according to the ninth aspect of the invention or a vector according to the eleventh aspect of the invention.

Preferably, the host cell is a bacterial cell or a yeast cell.

A thirteenth aspect of the invention provides an antibody-like molecule according to the fifth aspect of the invention or a compound according to the eighth aspect of the invention for use in medicine.

Exemplary uses of the antibody-like molecules and compounds of the invention in medicine include the use of said molecules and compounds in the prophylactic and/or therapeutic treatment of chronic inflammatory diseases, such as rheumatoid arthritis, Crohn's disease, multiple sclerosis and atherosclerosis.

The invention further provides a compound according to the third aspect of the invention for use in the treatment of a chronic inflammatory disease.

The antibody-like molecules and compounds of the invention may be delivered systemically or locally. They may be administered orally, intramuscularly, intravenously, intranasally or via the lung. In particular, they may be administered directly into the synovium (i.e. intra-articularly).

A further aspect of the invention provides the use of an antibody-like molecule according to the fourth aspect of the invention or a compound according to the third or eighth aspects of the invention in the preparation of a medicament for the treatment of a chronic inflammatory disease.

Preferably, the chronic inflammatory disease is rheumatoid arthritis.

A still further aspect of the invention provides a method of treating a patient with a chronic inflammatory disease comprising administering to said patient a therapeutically effective amount of an antibody-like molecule according to the fourth aspect of the invention or a compound according to the third or eighth aspects of the invention.

Yet another aspect of the present invention provides a pharmaceutical formulation comprising a monoclonal antibody or fragment thereof according to the fourth aspect of the inventions or a compound according to the third or eighth aspects of the invention and a pharmaceutically acceptable carrier. It will be appreciated that such formulations may be administered to a patient with a chronic inflammatory disease either alone or in combination with other therapeutic agents.

The formulations may conveniently be presented in unit dosage form and may be prepared by any of the methods well known in the art of pharmacy. Such methods include the step of bringing into association the active ingredient (i.e. compound of the invention) with a carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropyl-methylcellulose in varying proportions to provide desired release profile.

Formulations suitable for topical administration on the skin include creams, gels and ointments comprising the active ingredient and a pharmaceutically acceptable carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It will be understood that, in addition to the compounds particularly mentioned above, the formulations of this invention may include other agents conventional in the art having regard to the type of formulation in question, for example those suitable for oral administration may include flavouring agents.

A still further aspect of the invention provides. a preparation of T-cell enriched cells wherein the cells are from tissue from a site of inflammation in a patient suffering from a chronic inflammatory disease.

By "a preparation" of cells we include an isolated culture of such cells.

By "T-cell enriched" cells we mean a preparation of cells wherein the proportion of T cells relative to non-T cells has been increased compared to the proportion of T cells in said tissue in vivo. Preferably, the preparation of T-cell enriched cells contains 50% T cells, more preferably, 70%, 80%, 90%, 95% or 99% T-cells. Most preferably, the preparation of T-cell enriched cells contains only T cells.

Advatangeously, the patient has rheumatoid arthritis.
Conveniently, the tissue is taken from the synovium.
Preferably, the cells are isolated as follows:
(i) tissue from a site of inflammation in a patient suffering from a chronic inflammatory disease is provided;
(ii) cells from said tissue are suspended in culture medium;
(iii) T-cells are selectively isolated using anti-CD3 monoclonal antibodies; and
(iv) said CD3+ T-cells are re-suspended in culture medium.

Preferably, CD3+ cells are enriched by attachment to beads coated in anti-CD3+ monoclonal antibodies.

Alternatively, T cells may be enriched by negative selection of adherent cells and/or the positive selection of non-adherent cells (see Examples).

The present invention will now be described in more detail with reference to the following non-limiting figures and examples:

FIG. 1 shows the effect of a porous membrane insert on monocyte TNFα production induced by $T_{tcr}$ cells and $T_{ck}$ cells. Human peripheral blood T cells were isolated and cultured with either (A) anti-CD3 antibodies for 24 hours to selectively stimulate $T_{tcr}$ cells or (B) a cocktail of cytokines (IL-2, IL-6 and TNFα) for 8 days to selectively stimulate $T_{ck}$ cells. Following fixation, T-cells were incubated with monocytes (at a ratio of 5:1 T cells:monocytes) for 18 hours in the absence or presence of a porous membrane insert which physically separated the two cell populations in the tissue culture plate. In control experiments, separate cultures of monocytes and T cells were analysed. In addition, lipopolysaccharide (LPS, 10 ng/ml) was used as a positive control. In all experiments, culture supernatants were assayed for TNFα content. Data are expressed as means ±SD, and are representative of three experiments performed using different donors.

Figure 2:
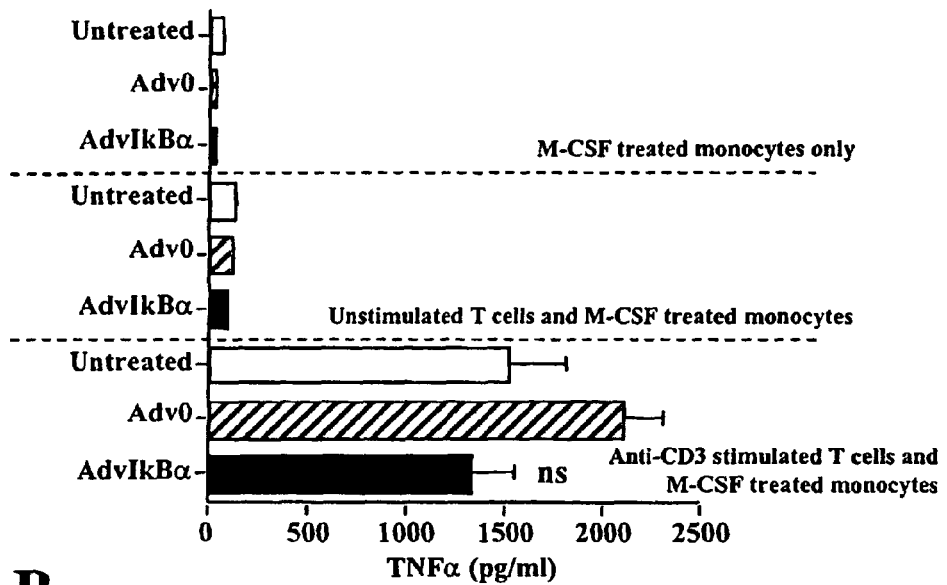
Figure 2:
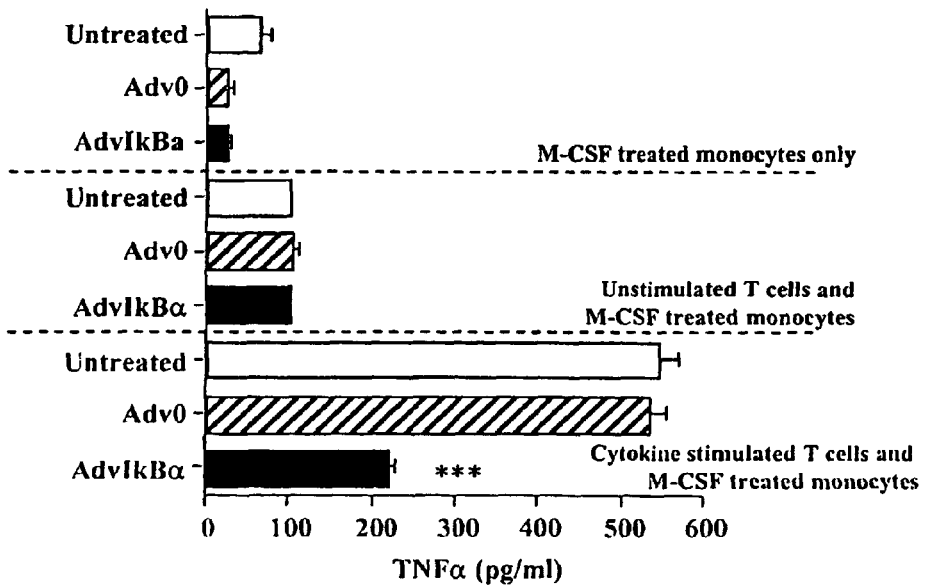

FIG. 2 shows the effect of over-expression of the NF-κB inhibitor, IκcBα, on monocyte TNFα production induced by $T_{tcr}$ cells and $T_{ck}$ cells. Human peripheral blood T cells were isolated and cultured in the absence of a stimulatory challenge ('unstimulated') or in the presence of (A) anti-CD3 antibodies for 24 hours to selectively stimulate $T_{tcr}$ cells or (B) a cocktail of cytokines (IL-2, IL-6 and TNFα) for 8 days to selectively stimulate $T_{ck}$ cells, prior to fixation. Monocytes were cultured with M-CSF (100 ng/ml) for 2 days prior to infection with adenovirus containing either IκBα (AdvIκBα) or no insert (Adv0), at a multiplicity of infection (m.o.i.) of 80:1. Fixed, activated T cells and M-CSF-treated monocytes were then co-cultured for 18 hours at a ratio of 5:1 (T cells: monocytes). In control experiments, M-CSF-treated monocytes were cultured in the absence of T cells. In all experiments, culture supernatants were assayed for TNFα content. Data are expressed as means ±SD, and are representative of three experiments performed using different donors. ***$p<0.001$.

Figure 3:
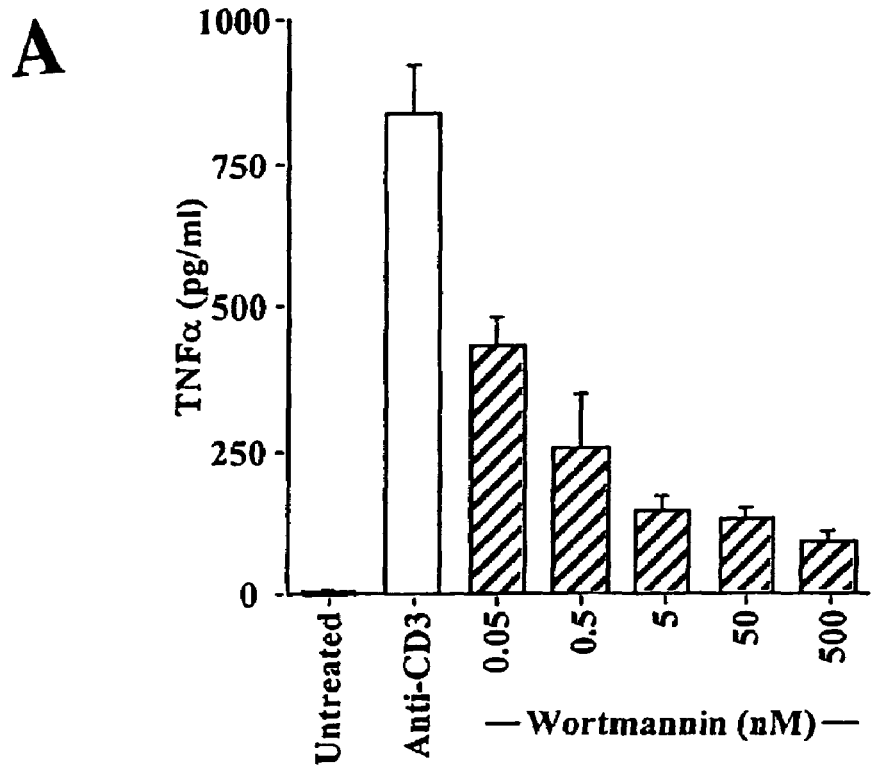
Figure 3:
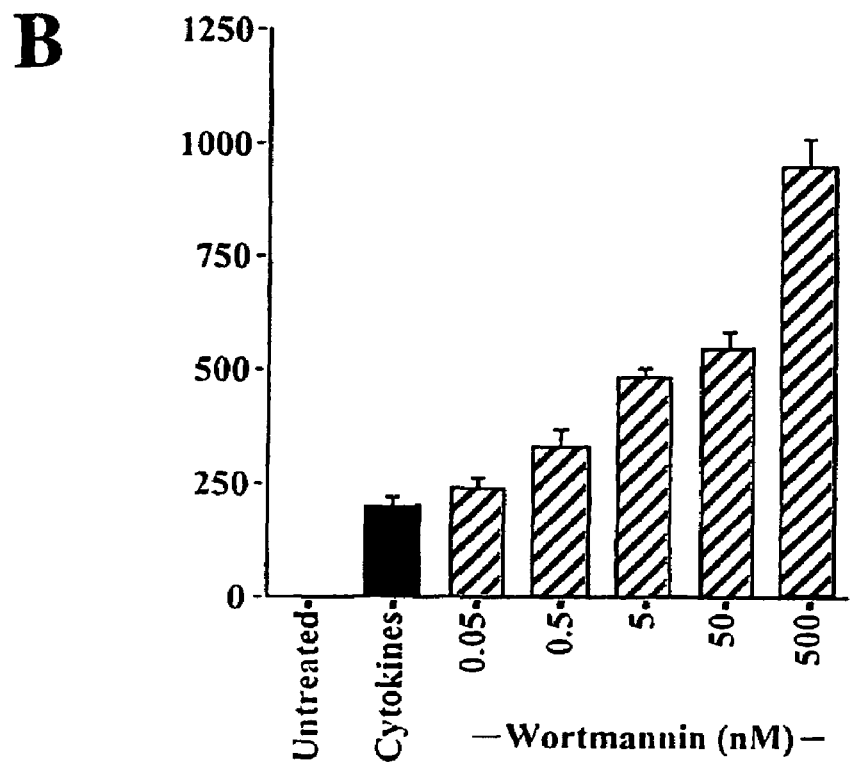
Figure 3:
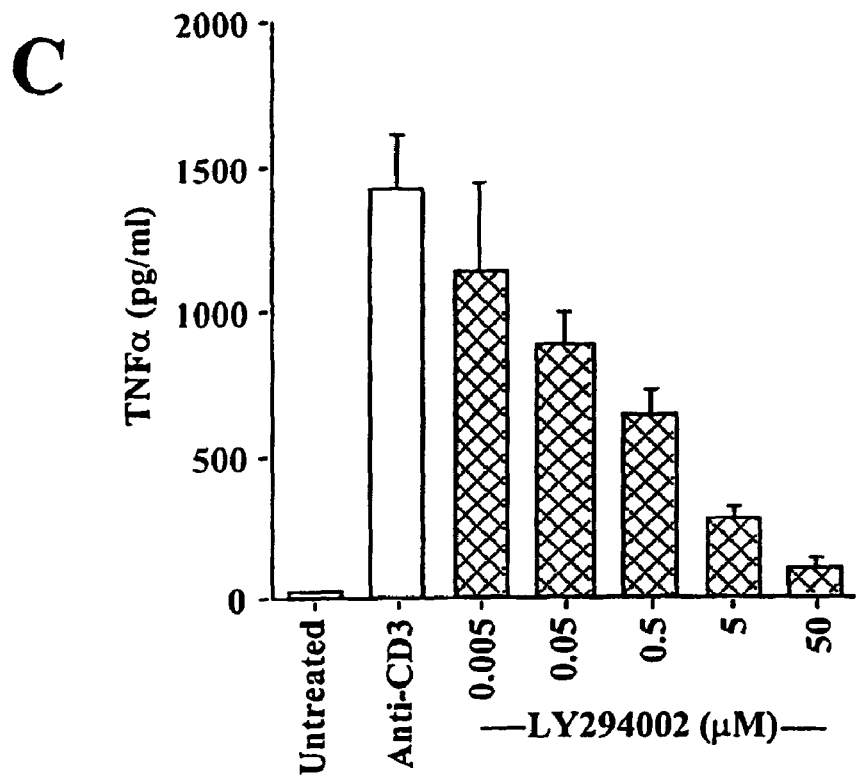
Figure 3:
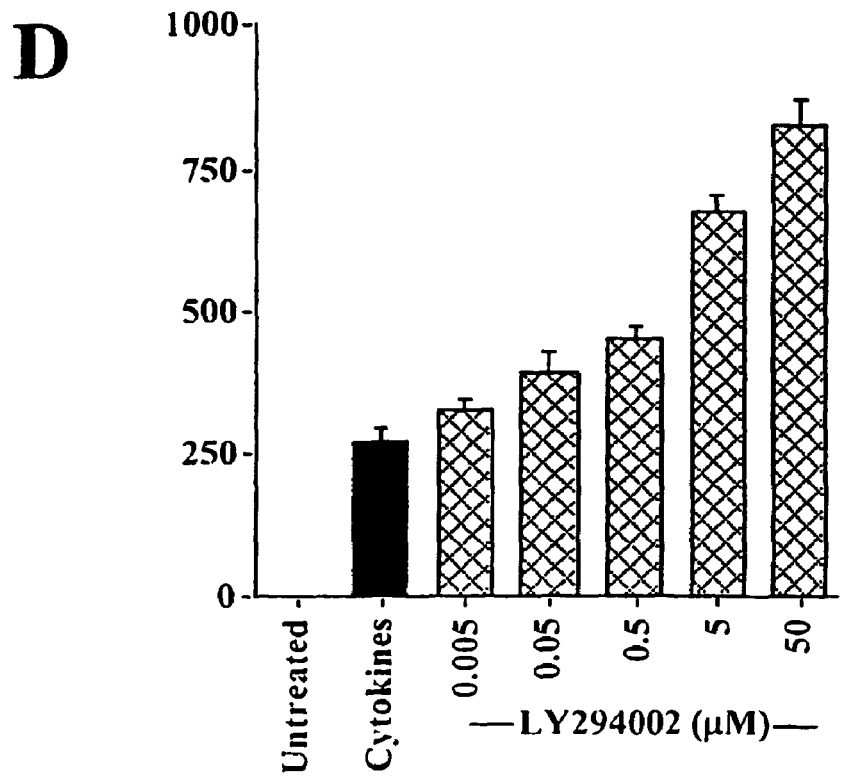

FIG. 3 shows the effect of PI3 kinase inhibitors on T cell-induced production of TNFα by monocytes. Human peripheral blood T cells were isolated and cultured with either (A and C) anti-CD3 antibodies for 24 hours to selectively stimulate $T_{tcr}$ cells or (B and D) a cocktail of cytokines (IL-2, IL-6 and TNFα) for 8 days to selectively stimulate $T_{ck}$ cells. Following fixation, T-cells were incubated with monocytes (at a ratio of 5:1 T cells:monocytes) for 18 hours in the presence of increasing concentrations of Wortmannin or LY294002. In all experiments, culture supernatants were assayed for TNFα content. Data are expressed as means ±SD, and are representative of three experiments performed using different donors.

Figure 4:
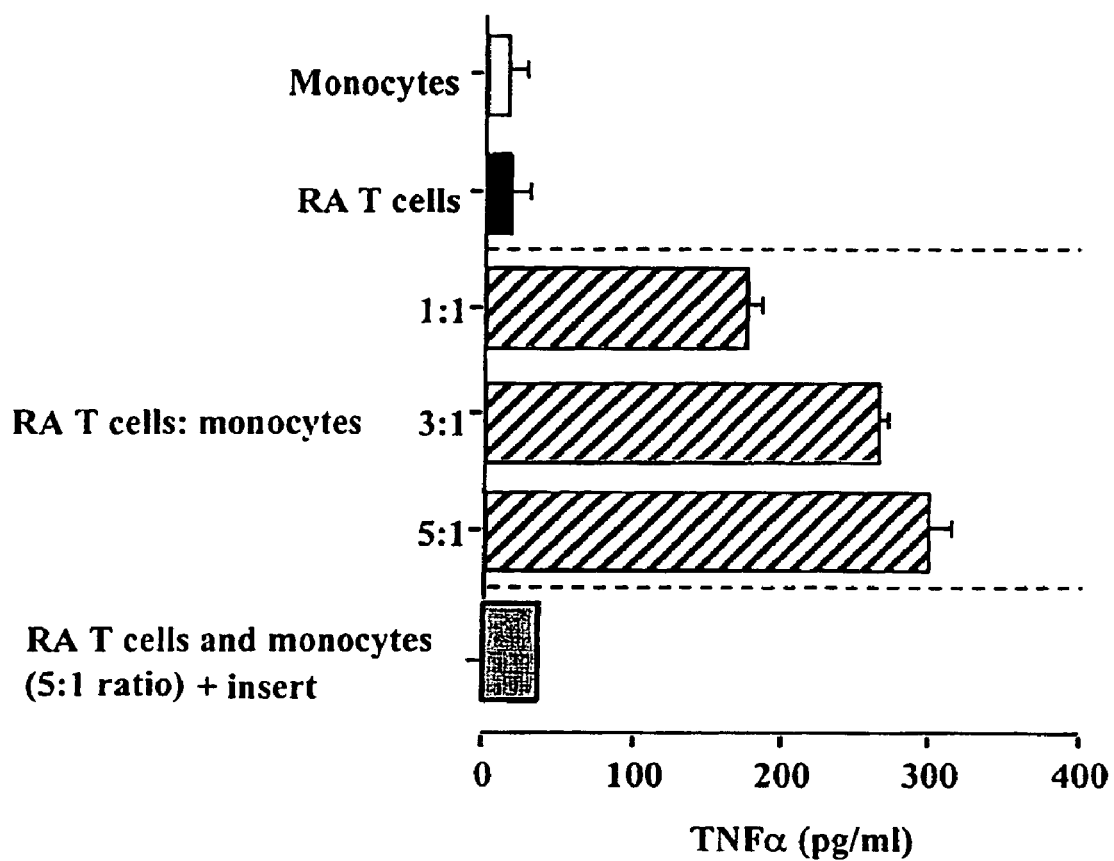

FIG. 4 shows the induction of monocyte TNFα production by T cells derived from rheumatoid arthritis (RA) synovial tissue. CD3+ enriched cells were isolated from RA synovial mononuclear cells by direct, positive selection on anti-CD3 antibody coated Dynabeads. Following fixation, RA T cells were incubated for 18 hours with normal monocytes at increasing ratios of T cells to monocytes, as indicated, and in the absence or presence of a porous membrane insert which physically separated the two cell populations in the tissue culture plate. In control experiments, separate cultures of monocytes and T cells were analysed. Culture supernatants were assayed for TNFα content. Data are expressed as means ±SD, and are representative of three experiments performed using different donors.

Figure 5:
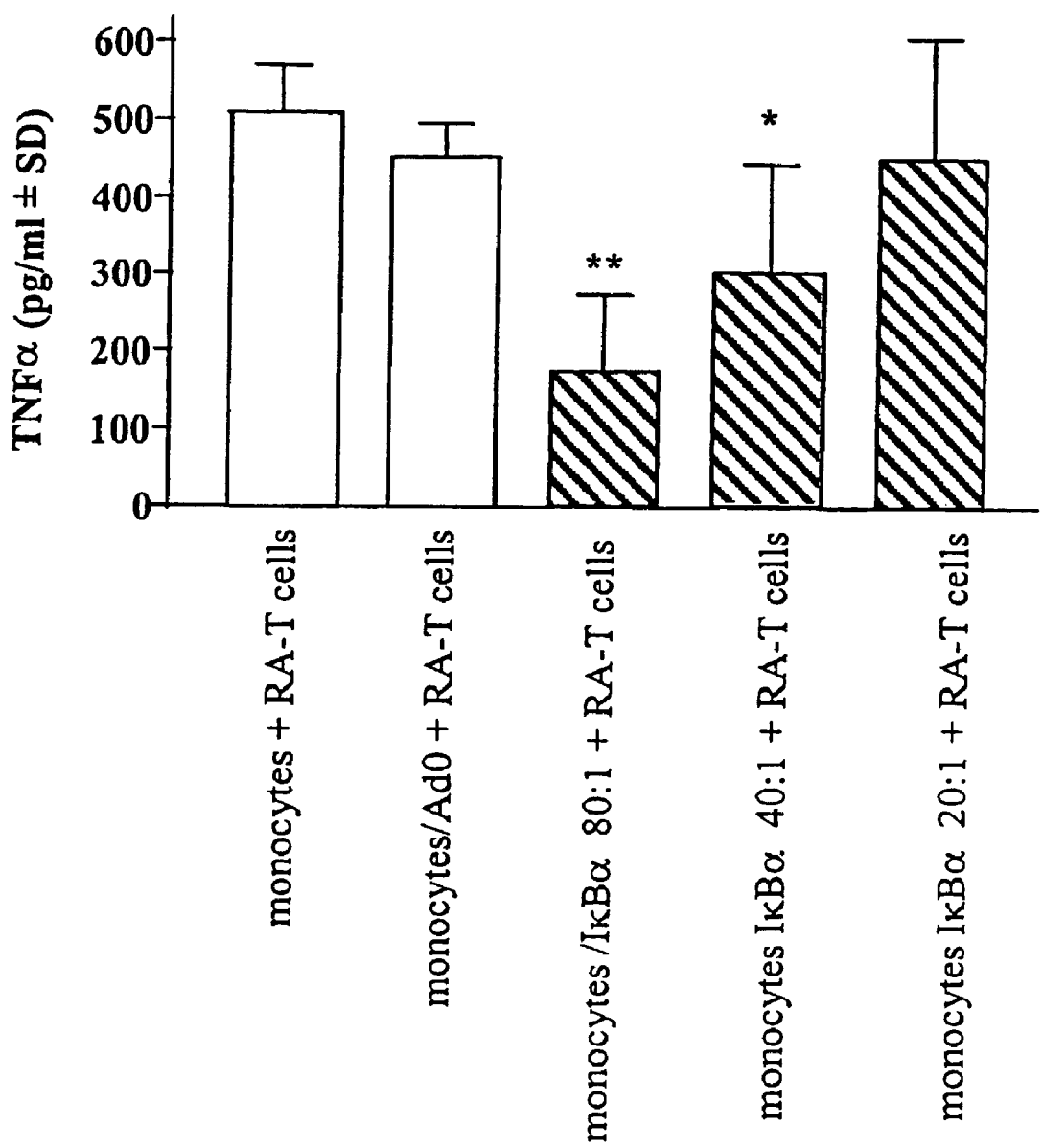
Figure 5:
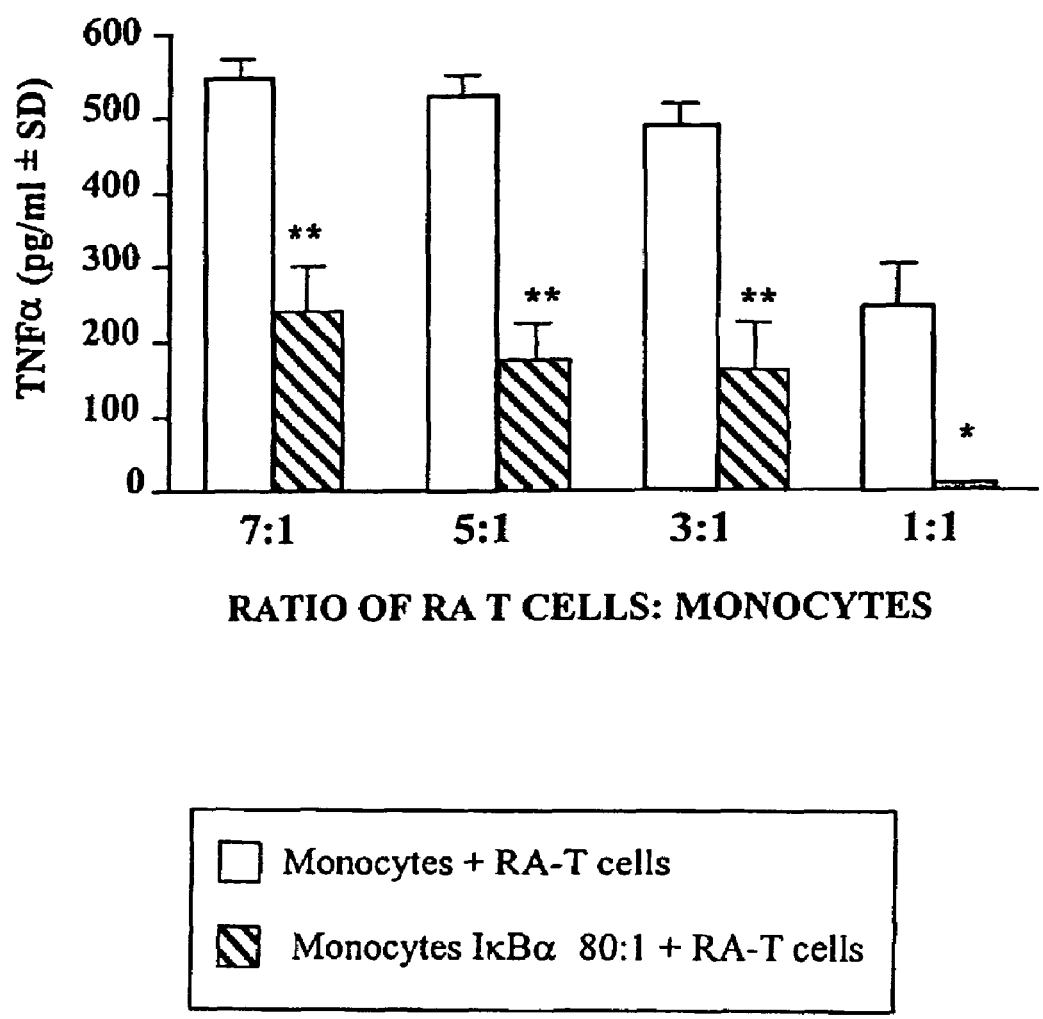

FIG. 5 shows the effect of over-expression of the NF-κB inhibitor, IκBα, on monocyte TNFα production induced by rheumatoid arthritis T cells. RA CD3+ enriched cells were isolated from RA synovial mononuclear cells by direct, positive selection on anti-CD3 antibody coated Dynabeads. Following fixation, RA T cells were incubated for 2 days (at a ratio of 3:1 T cells:monocytes) with normal monocytes treated with M-CSF (100 ng/ml) and then infected with adenovirus containing either IκBα (AdvIκBα) or no insert (Adv0) (m.o.i. from 20:1 to 80:1) (FIG. 5A). Following incubation for 18 hours, supernatants were harvested and assayed for TNFα content. In a separate experiment, RA T cells were incubated at different ratios with monocytes infected with adenovirus expressing IκcBα (m.o.i. 80:1) (FIG. 5B). Data are expressed as means ±SD, and are representative of three experiments performed using different donors. Statistical analysis of the results was performed using the Student's 2-tailed t-test. ** $p<0.01$, * $p<0.05$ compared with untreated or Ad0 groups.

Figure 6:
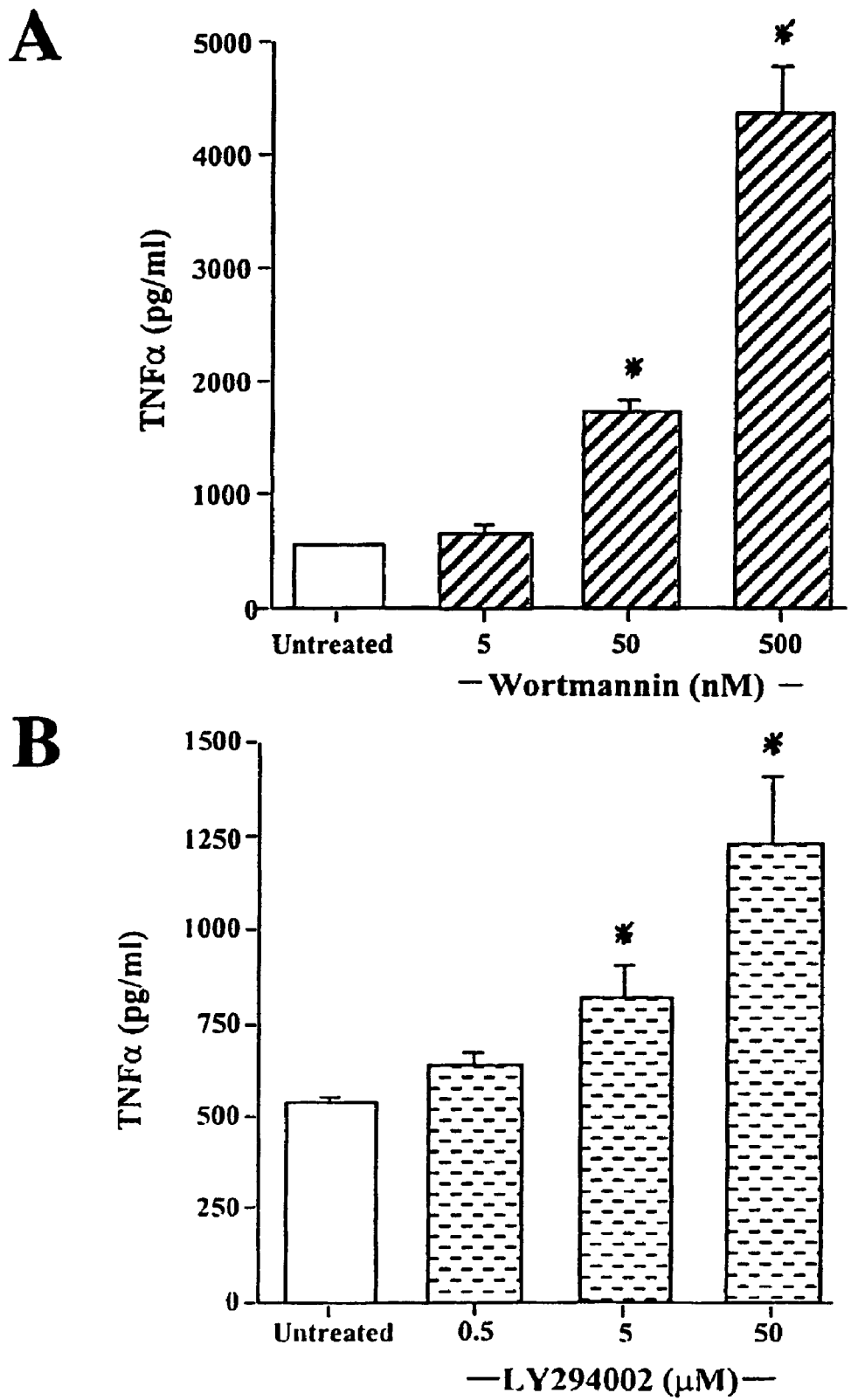

FIG. 6 shows the effect of PI3 kinase inhibitors on monocyte TNFα production induced by rheumatoid arthritis T cells. CD3+ enriched cells were isolated from RA synovial mononuclear cells by direct, positive selection on anti-CD3 antibody coated Dynabeads. RA cells ($1\times10^6$ cells/ml) were cultured in the absence ('untreated') or presence of increasing concentrations of (A) Wortmannin or (B) LY294002. In all experiments, culture supernatants were assayed for TNFα content. Data are expressed as means ±SD, and are representative of eight experiments performed.

Figure 7:
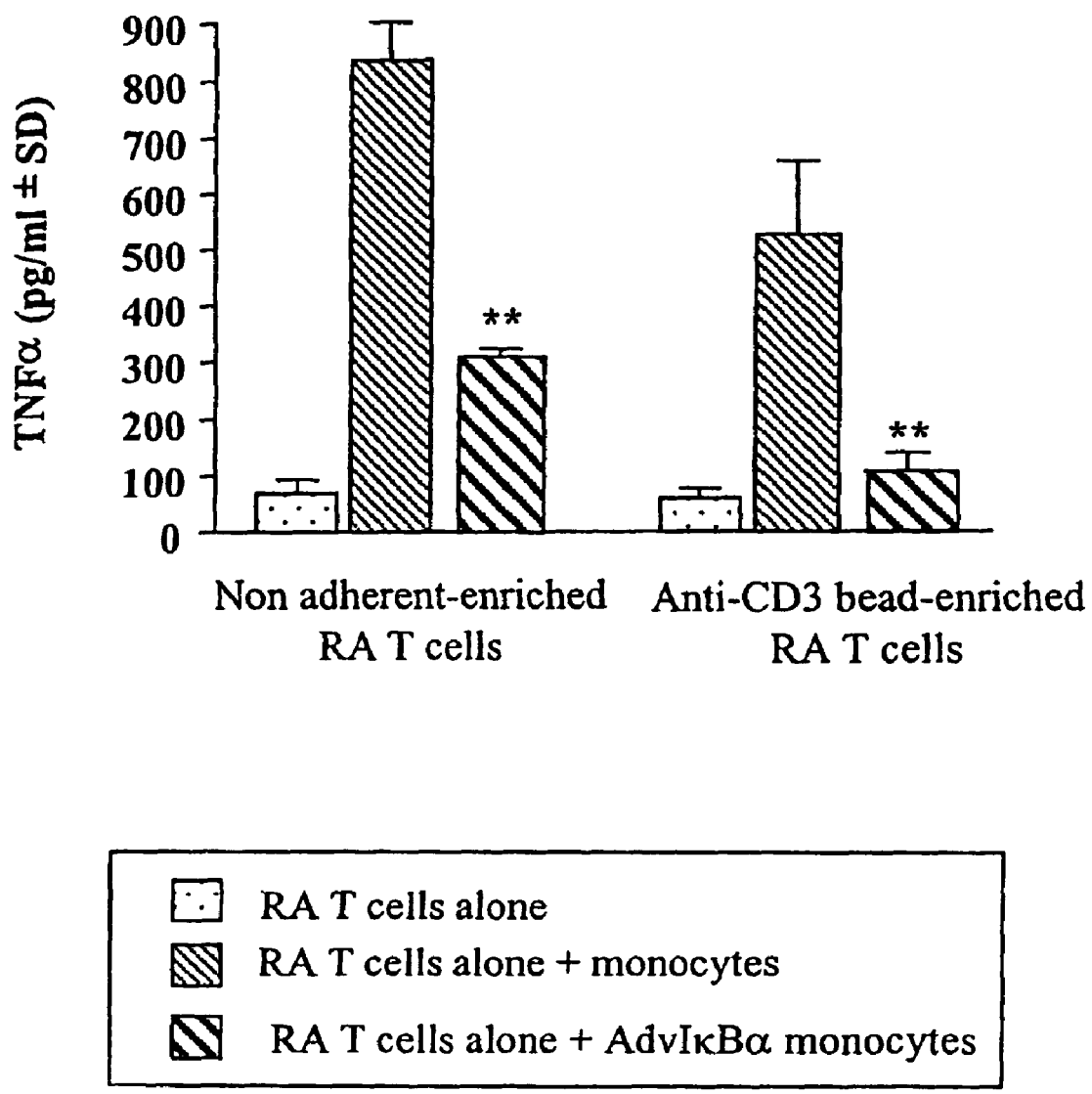

FIG. 7 shows the effect of over-expression of the NF-κB inhibitor, IκcBα, on monocyte TNFα production induced by non-adherent rheumatoid arthritis T cells. RA cells were isolated from RA synovial mononuclear cells by direct, positive selection on anti-CD3 antibody coated Dynabeads and by negative selection using the non-adherent population. Following fixation, RA T cells were incubated for 2 days with normal monocytes treated with M-CSF (100 ng/ml), at a ratio of 3:1 T cells:monocytes, and then infected with adenovirus containing either IκBα (AdvIκBα) or no insert (Adv0) (m.o.i. 80:1). Following incubation for 18 hours, supernatants were harvested and assayed for TNFα content. Data are expressed as means of triplicate cultures ±SD, from the same RA donor. Statistical analysis of the results was performed using the Student's 2-tailed t-test. ** $p<0.01$ compared with controls (i.e. monocytes stimulated with RA T cells).

EXAMPLES

T Cell and Monocyte Purification

Human peripheral blood T cells and monocytes were isolated from single donor plateletpheresis residues (purchased from the North London Blood Transfusion service, Colindale, GB). Mononuclear cells were isolated by Ficoll/Hypaque centrifugation (specific density 1.077 g/ml, Nycomed Pharma AS, Oslo, Norway), prior to cell separation in a Beckman JE6 elutriator. Elutriation was performed in culture medium containing 1% heat-inactivated foetal calf serum (FCS) using methods known in the art (see Sebbag et al., 1997, Parry et al., 1997). T cell and monocyte purity were assessed by flow cytometry (see Sebbag et al., 1997).

T cell fractions contained typically about 70% CD3-expressing cells, about 8% CD19-expressing cells, and less than 1% CD14-expressing cells. Monocyte fractions contained typically about 85% CD14-expressing cells, less than 0.5% CD19-expressing cells, and less than 3% CD3-expressing cells.

$T_{ck}$ and $T_{tcr}$ cells were generated from elutriation-enriched T cells as follows:

$T_{ck}$ cells: $T_{ck}$ cells were generated by culturing the elutriation enriched T cells at a density of $10^6$ cells/ml in RPMI 1640 (containing 10% heat inactivated AB+ human serum (Biowhittaker, UK) with saturating concentrations of a cocktail of TNFα (25 ng/ml), IL-6 (100 ng/ml) and IL-2 (25 ng/ml) for 8 days in culture prior to fixation.

$T_{tcr}$ cells: $T_{tcr}$ cells were prepared from elutriation enriched T cells by resuspending the cells at a density of $10^6$ cells/ml in RPMI 1640 (containing 10% heat inactivated AB+ human serum (Biowhittaker, UK). Following resuspension, the cells were incubated (at 37° C. in a 5% $CO_2$/95% humidified incubator) in 6-well culture plates with immobilised anti-CD3 monoclonal antibodies for 24 hours (OKT3, ATCC, Maryland, USA), the antibodies having previously been coated on to the 6-well culture plates at 10 μg/ml (overnight at 4° C.).

Following completion of the culture period, the $T_{ck}$ and $T_{tcr}$ cells were harvested and washed three times in RPMI medium containing 1% heat-inactivated fetal calf serum (FCS), prior to fixation for 1 minute at 0° C. in PBS containing 0.05% glutaraldehyde, and neutralized with an equivalent volume of T lymphocyte neutralizing buffer containing 0.2 M glycine.

Control populations of T cells were cultured in the absence of any cytokine (for experiments with $T_{ck}$ cells), or were fixed immediately after isolation from peripheral blood (for experiments with $T_{tcr}$ cells).

Isolation of Rheumatoid Arthritis Synovial Mononuclear Cells and Enrichment of CD3+ Cells Rheumatoid arthritis (RA) mononuclear cells were obtained from synovial tissue specimens provided by the Rheumatology Clinic, Charing Cross Hospital, London, UK. Tissue was teased into small pieces and digested in medium containing 0.15 mg/ml DNase type 1 (Sigma, UK) and 5 mg/ml collagenase (Roche, UK) for 1 to 2 hours at 37° C. After passing cells through nylon mesh to exclude cell debris, cells were washed and resuspended in RPMI medium (Biohittaker, Verviers, Belgium) (containing 10% heat-inactivated FCS) at a density of $1\times10^6$ cells/ml and used immediately.

CD3+ enriched cells were isolated from RA synovial mononuclear cells by direct, positive selection using Dynabeads (Dynal UK Ltd, Wirral, UK) coated with anti-CD3 monoclonal antibodies (anti-CD3 mAbs). Briefly, mononuclear cells ($1\times10^7$) were cultured with 100 μl anti-CD3 mAb-coated Dynabeads for 20 minutes at 4° C. under constant rotation. Cells attached to beads were isolated using a magnetic particle concentrator (Dynal, Merseyside, UK) and cultured for 6 hours at 37° C. Detached cells were removed from magnetic beads and washed three times using the magnetic particle concentrator.

This technique allowed for isolation of CD3+ cells, yielding cells of high purity (>99%) and viability (>95%). Following isolation, CD3+ enriched cells were washed three times in RPMI medium containing 1% heat-inactivated FCS, fixed for 1 minute at 0° C. in phosphate-buffered saline (PBS) containing 0.05% glutaraldehyde, and neutralized with an equivalent volume of T lymphocyte neutralizing buffer containing 0.2 M glycine. Following a further three washes, the fixed CD3+ cells were resuspended (at a concentration of $2 \times 10^6$ cell/ml) in RPMI medium containing 5% heat-inactivated FCS, and stored for up to 7 days at 4° C. until used. Prior to use, CD3+ enriched cells were washed twice in complete medium.

In one experiment, the non-adherent population of RA cells was used (see FIG. 7). Non-adherent cells were prepared by culturing RA mononuclear cells in RPMI 1640 (containing 5% heat inactivated FCS) at $2 \times 10^6$ cells/ml in a 24-well plate. After one hour at 37° C., the non-adherent cell population (i.e. those cells not attached to the plate) was removed from the culture plate by pipette, washed in RPMI (containing 1% heat inactivated FCS), and incubated overnight at 37° C. Following isolation, the non-adherent cells were washed three times in RPMI medium containing 1% heat-inactivated FCS, fixed for 1 minute at 0° C. in phosphate-buffered saline (PBS) containing 0.05% glutaraldehyde, and neutralized with an equivalent volume of T lymphocyte neutralizing buffer containing 0.2 M glycine. Following a further three washes, the fixed non-adherent cells were resuspended (at a concentration of $2 \times 10^6$ cell/ml) in RPMI medium containing 5% heat-inactivated FCS, and stored for up to 7 days at 4° C. until used. Prior to use, non-adherent cells were washed twice in complete medium.

Isolation of Osteoarthritis Synovial Mononuclear Cells and Enrichment of CD3+ Cells Osteoarthritis (OA) mononuclear cells were obtained from synovial tissue specimens provided by the Rheumatology Clinic, Charing Cross Hospital, London, UK. As in the case of RA cells (above), OA synovial tissue was teased into small pieces and digested in medium containing 0.15 mg/ml DNase type 1 (Sigma, UK) and 5 mg/ml collagenase (Roche, UK) for 1 to 2 hours at 37° C. After passing cells through nylon mesh to exclude cell debris, cells were washed and resuspended in RPMI medium (BioWhittaker, Verviers, Belgium) (containing 10% heat-inactivated FCS) at a density of $1 \times 10^6$ cells/ml and used immediately.

As described previously (see Brennan et al, 1989, *Lancet* 2:244-247), the majority of cells in OA synovial tissue are non-haematopoetic, with very few lymphocytes. Indeed, in the OA synovial tissue used in the experiments described, the proportion of CD45 +ve cells was 28% and the proportion of CD3 +ve cells was 4%. For this reason, anti-CD3 antibody coated beads were not used to deplete the T cells, instead the macrophage population was negatively enriched by removing the non-adherent cells from the culture.

Adherent cells were enriched by culturing OA mononuclear cells in RPMI 1640 (containing 5% heat inactivated FCS) at $2 \times 10^6$ cells/ml in a 24-well plate. After one hour at 37° C., the non-adherent cell population (i.e. those cells not attached to the plate) was removed from the culture plate by pipette. The adherent cell population constituted those cells still adhering to the plate after removel of the non-adherent cells. The adherent cells were incubated at 37° C. for a further 18 hours in RPMI (containing 5% heat inactivated FCS), after which time supernatants were harvested and assayed for TNFα production by ELISA.

FACS Staining

Elutriation fractions, RA synovial membrane cells and enriched RA CD3+ ve cells were phenotyped using fluorescent conjugated antibodies and analyzed by flow cytometry. In brief, cells ($1 \times 10^5$/condition) were washed twice in FACS buffer (PBS containing 2% (v/v) FCS and 0.02% sodium azide), pelleted and blocked with 20% human serum. This step and all subsequent incubations were performed for 30 minutes on ice, and the cells washed thrice in FACS buffer after each step. Aliquots were incubated with conjugated anti-CD69 FITC, anti-CD4, anti-CD3 FITC, anti-CDS FITC, anti-CD2 FITC, anti-HLA class 11-FITC, CD45RA-PE, anti-CD45RO-PE (Pharmingen, Calif., USA) or CD14-FITC/CD45-PE, CD3-FITC/CD19-PE (Becton Dickinson, Calif., USA) (H+L) antibody (PE; Southern Biotechnology Associates, USA) or fluorescein isothiocyanate (FITC; Southern Biotechnology Associates, USA). Samples were analyzed using the Becton Dickinson Facscan flow cytometer.

Monocyte Culture

Monocytes were cultured at $1 \times 10^6$ cells/ml in RPMI 1640 medium (containing 5% heat-inactivated FCS) in round-bottomed 96-well culture plates (Nunc Life Technologies Ltd., Paisley, Scotland) in the presence of fixed T cells at varying T-cell/monocyte ratios ranging from 1:1 to 7:1 (as indicated). In some experiments, a semi-permeable membrane insert (Nunc Life Technologies Ltd., Paisley, Scotland) was fitted into the culture wells to physically separate the monocytes from the T cells. In all experiments, efficient fixation of T cells was tested by incubating an aliquot of T-cells ($7 \times 10^6$ cells/ml) in the absence of monocytes and assaying the amount of TNFα released by the cells under these conditions. Lipopolysaccharide (LPS, 10 ng/ml) was included in experiments as a positive control for monocyte cytokine production.

After 18 hour incubation at 37° C. with 5% $CO_2$, culture supernatants were harvested and stored at −20° C. until assayed by ELISA. All experiments were performed at least three times, and the figures show representative examples of these experiments.

Measurement of Cytokines by Sandwich ELISA

Reagents for the TNFα ELISA were provided by Dr. W. Buurman (Rijks Universiteit Limburg, Maastricht, Netherlands). The ELISA was performed using immobilized anti-TNFα mAb 61E71. and developed using a rabbit anti-TNFα polyclonal antibody. An alternative ELISA for TNFα is commercially available from Pharmingen. The rabbit polyclonal antibody was detected using a peroxidase-conjugated goat anti-rabbit IgG (H+L) (Jackson Immunoresearch Laboratories Inc., Westgrove, PE, USA) followed by an appropriate substrate. The sensitivity range of the assay was 1.6 to 5000 pg/ml.

Enzyme Inhibitor Studies

In all enzyme inhibitor experiments with RA synovial membrane cells, supernatants were harvested at 48 hours since this was found to be optimal for the production of TNFα. Enzyme inhibitors were added to cultures of RA synovial membrane cells for 48 hours at 37° C.

For monocyte/T-cell co-culture experiments, monocytes were cultured with relevant enzyme inhibitors at 37° C. for varying periods of time (see legend to Table 2) prior to co-culture with fixed T-cells for 18 hours. Supernatants were harvested and assayed for presence of TNFα by ELISA. Cell suspensions were taken for determination of cell viability.

Analysis of Cell Viability

Cell viability was assessed using an MTT assay (3-(4,5-dimethylthiazol-2-yl)-2,5-diphenyltetrazolium bromide), as described by Denizot and Lang (1986) *J Immunol Methods* 89(2), 271-7.

Characterisation of $T_{tcr}$ Cell- and $T_{ck}$ Cell-Induced TNFα Production by Monocytes Normal peripheral blood T cells were isolated as described above and activated by stimulation with either (i) immobilized anti-CD3 antibodies (OKT3, ATCC, Maryland, USA) for 24 hours, or (ii) a combination of cytokines (IL-2, IL-6 and TNFα) for a period of 8 days, prior to fixation. Both stimulatory challenges induced TNFα production by monocytes in a dose dependent manner, with a co-culture cell ratio of 7:1 (T cells: monocytes) being optimal (data not shown).

Inclusion of a porous membrane insert, which physically separated the two cell populations, significantly reduced TNFα production in monocytes co-cultured with T cells (T cell:monocyte ratio of 5:1) in response to activation with either anti-CD3 antibodies or the combination of cytokines (FIG. 1), indicative of the need for cell-cell interactions between T cells and monocytes.

Using the T cell selective stimulatory challenges described above, the $T_{tcr}$ cell- and $T_{ck}$ cell-induced TNFα production by monocytes was characterised as follows:

(i) Over-expression of IκBα inhibits TNFα production in monocytes induced by cytokine stimulated T cells ($T_{ck}$ cells)

TNFα production by monocytes/macrophages in response to certain stimuli is dependent on the activity of the transcription factor NF-κB. For example, adenoviral gene transfer of the inhibitor of NF-κB (AdvIκBα) has been shown to inhibit lipopolysaccharide- but not zymosan-induced TNFα (Bondeson et al., 1999, *J. Immunol.* 162, 2939-2945). Hence, the involvement of NF-κB in monocyte TNFα production induced by $T_{tcr}$ and $T_{ck}$ cells was evaluated.

Monocytes were treated with M-CSF for 2 days as described above, infected with adenovirus containing either an insert encoding IκBα (AdvIκBα) or no insert (Adv0). The effect of IκBα over-expression on T cell-induced monocyte (ratio 5:1) TNFα production was then determined.

Data presented in FIG. 2 demonstrate that over-expression of IκBα significantly p<0.001) reduced TNFα production by 60% from 550 pg/ml (Adv0 controls) to 220 pg/ml (AdvIκBα) in M-CSF treated monocytes stimulated by cytokine activated T cells (ie. $T_{ck}$ cells activated by incubation with IL-2, IL-6 and TNFα). In contrast, over-expression of IκBα had little effect on TNFα production in M-CSF monocytes infected with AdvIκBα (1400 pg/ml) compared with untreated Adv0 controls (1500 pg/ml) when stimulated with anti-CD3 antibody activated T cells (i.e. $T_{tcr}$ cells).

(ii) PI3 kinase inhibitors attenuate monocyte TNFα production stimulated by $T_{tcr}$ cells but enhance monocyte TNFα production stimulated by $T_{ck}$ cells The effect of the PI3 kinase inhibitors, wortmannin and LY294002, was investigated on T cell-induced TNFα production by monocyte. Wortmannin and LY294002 significantly inhibited monocyte TNFα production induced by anti-CD3 antibody stimulated T-cells (i.e. $T_{tcr}$ cells) in a dose dependent manner (FIGS. 3*a* and 3*c*). The $IC_{50}$ values for wortnannin (0.05 nM) and LY294002 (0.07 μM) were indicative of this being a PI3 kinase-mediated event.

In contrast, wortmannin and LY294002 significantly enhanced monocyte TNFα production (by about 3-4 fold) induced by cytokine stimulated T cells (i.e. $T_{ck}$ cells) (FIGS. 3*b* and 3*d*) in a similar manner to that previously observed with LPS.

Kinase p70 S6 is a downstream effector of PI3 kinase (Monfar et al., 1995, *Mol. Cell. Biol.* 15:326-337), the activity of which can be blocked with the drug rapamycin. Rapamycin was found to have no effect on monocyte TNFα production induced by either cytokine stimulated (IL-2, IL-6 and TNFα) or anti-CD3 antibody stimulated T cells (results not shown).

In addition to inhibiting PI3 kinase activity, the fungal product wortmannin has also been shown to inhibit other signalling pathways, including phospholipase $A_2$ ($PLA_2$) (Cross et al., 1995). To test whether the effect of wortmannin on $T_{ck}$ cell- and $T_{tcr}$ cell-induced TNFα production by monocytes involved the $PLA_2$ signalling pathway, the effect of a second $PLA_2$ inhibitor, arachidonyl trifluoromethyl ketone analogue (AKTA), was tested.

Unlike LPS-induced stimulation of monocytes, AKTA had no effect on TNFα production following stimulation with T-cells cultured with either anti-CD3 antibodies or cytokines (IL-2, IL-6 and TNFα) (results not shown). These observations indicate that the effect of wortmannin on $T_{ck}$ cell- and $T_{tcr}$ cell-induced TNFα production by monocytes is not mediated by $PLA_2$ TNFα Production in Synovial Fluid From Rheumatoid Arthritis (RA) Patients: Identification of the T cell Subtypes Involved Experiments were performed to investigate whether T cells enriched from RA synovial tissue could induce TNFα synthesis in normal resting monocytes without further activation (i.e. without incubation with anti-CD3 antibodies or a cocktail of cytokines). T cells were enriched from RA synovial mononuclear cells (MNC) using anti-CD3 'detach a bead' at 4° C. as described above. In replicate experiments (n=3), RA CD3+ ve T cells were found to be predominantly CD4+ CD45RO+, although CD8+ and CD45RA cells were also present. The T cell activation markers, HLA-DR and CD69 were also present, suggesting that RA CD3+ cells were of the "memory" phenotype and activated (see Table 1).

TABLE 1

| Surface Marker | % cells stained |
| --- | --- |
| CD4 | 58 |
| CD8 | 30 |
| CD2 | 80 |
| CD69 | 60 |
| CD45RA | 10 |
| CD45RO | 85 |
| HLA-DR | 53 |

Table 1 shows the cellular phenotype of RA CD3-positive cells.

RA CD3-positive cells were isolated from RA synovial mononuclear cells by direct, positive selection on anti-CD3 antibody coated Dynabeads. FACS analysis was performed using a Becton Dickinson Facscan flow cytometer. Data are presented as percentage of stained cells compared with isolated matched controls, and are representative of two experiments using different donors.

Monocytes isolated by elutriation were cultured with fixed RA CD3+ enriched cells for 18 hours. Data presented in FIG. 4 demonstrate that RA CD3+ cells induced TNFα production in normal monocytes in a dose dependent manner with a T cell:monocyte ratio of 5:1 being the most effective (inducing 300 pg/ml TNFα). Fixed RA CD3+ enriched cells cultured alone released negligible TNFα, barely above the limit of detection in the ELISA (50 pg/ml). Furthermore, monocyte derived TNFα induced by fixed RA CD3+ enriched cells was inhibited by about 90% when the two cell populations were physically separated, preventing any contact-mediated events from occurring.

In addition, TNFα levels were significantly reduced in RA synovial cultures in which the CD3+ ve T cells had been depleted. Specifically, TNFα levels in 2-day cultures were reduced by 71% from 512 pg/ml in the total synovial cell cultures to 148 pg/ml in the cell-depleted culture (data not shown). At 5 days in culture, the total synovial cell population produced 151 g/ml TNFα with less than 20 pg/ml produced in the T cell-depleted cultures.

Following the characterisation of $T_{tcr}$ cell- and $T_{ck}$ cell-induced TNFα production by monocytes described above, further experiments were performed to identify which subtype(s) of T cell were involved in TNFα production in RA synovial fluid.

(i) Effect of over-expression of IκBα on monocyte TNFα production induced by T cells derived from RA synovial tissue.

It had previously been demonstrated that the spontaneous production of TNFα in RA synovial tissue cultures was inhibited (by more than 80%) following blockade of the transcription factor NF-κB, using an adenovirus over-expressing the inhibitor IkBa (Foxwell et al., 1998). As blockade of NF-κB with an adenovirus expressing IκBα also discriminated between $T_{ck}$ and $T_{tcr}$ cell-induced monocyte TNFα production, comparable experiments were performed to determine whether NF-κB played an important regulatory role in the production of TNFα in normal peripheral blood monocytes stimulated with fixed RA T cells.

Peripheral blood monocytes were treated with M-CSF for 2 days to enable infection with either empty adenovirus (Adv0) or with adenovirus expressing IκBα (multiplicity of infection, or m.o.i., from 20 to 80:1). RA T cells were enriched from RA synovial tissue as described above, fixed and co-cultured with adenovirus-infected monocytes at a T cell:monocyte ratio of 3:1 for 18 hours.

Monocyte TNFα production induced by RA CD3+ enriched cells was inhibited by more than 70% p<0.0001) when the monocytes were infected with adenovirus over-expressing IκBα (m.o.i 80:1) (FIG. 5). TNFα levels in IκBα-infected monocytes stimulated with RA T cells were 83±11 pg/ml compared with 300±12 pg/ml in Adv0-infected monocytes (p<0.0001). At a m.o.i. of 40:1, TNFα production was also inhibited (>50%) but, due to insufficient RA T cells, this point was not performed in triplicate and hence statistical analysis could not be performed. No effect was observed with a m.o.i of 20:1. Thus, monocyte TNFα production induced by RA CD3+ enriched cells was similar to that induced by $T_{ck}$ cells and spontaneous TNFαproduction in RA synovial joint cells but was unlike that induced by anti-CD3 antibody stimulated $T_{tcr}$ cells.

As a positive control, monocytes from the same elutriation were also infected with adenovirus overexpressing IκBα and stimulated with LPS. As reported previously (Foxwell et al., 1998), over-expression of IκBα at a m.o.i. of 80:1 inhibited LPS-induced TNFα from 3497±805 pg/ml to 1025±235 p,,/ml (data not shown).

(ii) Effect of PI3 kinase inhibitors on TNFα production in RA synovial cultures and RA T cell-induced monocytes Since PI3 kinase inhibitors were found to discriminate between $T_{ck}$ and $T_{tcr}$ induced monocyte TNFα production, experiments were performed to determine whether PI3 kinase played a regulatory role in the spontaneous production of TNFα from RA synovial joint cell cultures. The PI3 kinase inhibitors, worttnannin (FIG. 6a) and LY294002 (FIG. 6b), both dose-dependently enhanced spontaneous TNFα production in total RA synovial membrane cultures from eight individuals.

The effect of wortmannin and LY294002 was also studied on monocyte TNFα production induced by RA CD3+ ve enriched cells (see Table 2). Normal monocytes isolated by elutriation were treated with selective enzyme inhibitors for the designated times prior to co-culture with fixed rheumatoid CD3+ T cells at a ratio 5:1 (T cells to monocytes) for 18 hours. Due to the limited number of RA CD3+ enriched cells, only one concentration of each inhibitor was used, i.e. the concentration shown to maximally inhibit monocyte TNFα production induced by fixed activated T cells. Unlike anti-CD3 antibody stimulated T cells, but similar to cytokine stimulated T cells and the spontaneous production of TNFα in RA synovial joint cells, TNFα production induced by RA CD3+ enriched cells was enhanced by wortmannin and LY294002. Thus, TNFα levels were increased from 686±59 pg/ml to 7333±304 pg/ml with wortmannin (500 nM), and from 686±59 pg/ml to 883±304 pg/ml with LY294002 (50 μM).

Experiments were also performed to determine whether the $PLA_2$, AKTA, displayed similar effects on TNFα synthesis to that of wortmannin. Consistent with $T_{ck}$ cell-induced stimulation of monocytes, AKTA had no effect on TNFα production in monocytes stimulated by RA T-cells (Table 2). Furthermore, the inclusion of rapamycin (10 μM) had no significant effect on TNFα synthesis.

TABLE 2

| Inhibitor | TNFα (pg/ml) | Percent change |
| --- | --- | --- |
| Untreated (control) | 686 ± 59 | — |
| LY294002 (50 μM) | 883 ± 38 | +29% |
| Wortmannin (500 nM) | 7333 ± 304 | +968% |
| AKTA (5 mM) | 606 ± 16 | −11% |
| Rapamycin (10 μM) | 399 ± 21 | −42% |

Table 2 shows the effect of incubation with LY294004, wortmannin, AKTA and rapamycin on monocyte TNFα production induced by rheumatoid arthritis T cells.

CD3+ enriched cells were isolated from RA synovial mononuclear cells by direct, positive selection on anti-CD3 antibody coated Dynabeads. Following fixation, RA T cells were incubated for in the absence ('untreated') or presence of LY294002 (50 μM, 30 minutes), Wortmannin (500 nM, 30 minutes), AKTA (5 mM, 30 minutes) or Rapamycin (10 μM, 60 minutes). RA T cells were then co-cultured with monocytes for 18 hours at a ratio 5:1 (T cells to monocytes). Culture supernatants were assayed for TNFα content. Data are expressed as means ±SD, and are representative of three experiments performed using different donors.

(iii) Effect of over-expression of IκBα on monocyte TNFα production stimulated with CD3+ ve and non-adherent populations of RA T cells Further experiments were conducted to determine the effect of over-expression of IκBα on TNFα production in monocytes following stimulation with T cells from RA synovial tissues. In these experiments, two populations of T cells were use, a CD3 +ve enriched population of T cells and a non-adherent population of T cells.

In both cases, T cell stimulated production of TNFα by monocytes was significantly inhibited by pre-incubation of the monocytes with adenovirus over-expressing the NF-κB inhibitor, IκBα (see FIG. 7). This finding is consistent with the $T_{ck}$ cells playing a key role in TNFα production in RA synovial tissue.

These data are also important because they indicate that the manner of isolation of T cells from RA synovial tissue does not influence the results obtained.

TNFα Production in Synovial Fluid from Osteoarthritis (OA) Patients: Effect of Incubation with the PI3 Kinase Inhibitor LY294002

For comparison with RA synovial tissue, experiments were performed to determine whether TNFα production in synovial tissue from a second degenerative joint disease, osteoarthritis, was also T cell dependent.

The effect of the PI3 kinase inhibitor, LY294002, was studied on TNFα production in osteoarthritis (OA) synovial cultures. OA synovial joint cultures were cultured for 48 hours in the presence of increasing concentrations of the PI3 kinase inhibitor, LY294002. Culture supernatants were then harvested and assayed for TNFα (pg/ml) by ELISA. Results (mean of triplicate cultures ±SD) are shown in Table 3.

TABLE 3

| | TNFα production (pg/ml) LY 294002 concentration (µM) | | | | | |
|---|---|---|---|---|---|---|
| Culture | 0.0 | 0.005 | 0.05 | 0.5 | 5.0 | 50.0 |
| OA 1833 | 224 ± 15 | 236 ± 11 | 235 ± 22 | 233 ± 28 | 202 ± 15 | 204 ± 5 |
| OA 1840 | 635 ± 19 | 612 ± 13 | 642 ± 32 | 597 ± 38 | 651 ± 50 | 600 ± 31 |
| OA 1851 | 227 ± 19 | 236 ± 13 | 250 ± 12 | 237 ± 63 | 233 ± 15 | 246 ± 19 |
| OA 1861 | 155 ± 42 | 141 ± 33 | 127 ± 5 | 145 ± 29 | 131 ± 44 | 215 ± 9 |
| OA 1862 | 141 ± 35 | 166 ± 31 | 171 ± 55 | 185 ± 7 | 226 ± 100 | 205 ± 19 |

Data in Table 3 indicate that the addition of varying concentrations of the PI3 kinase inhibitor, LY294002, to cultures of OA synovial tissue from five different samples had no significant effect on TNFα production. Thus, unlike in RA TNFα induction by $T_{ck}$ cells appears not to play a key role in OA.

In addition, removal of the non-adherent population of cells from the OA synovial cultures had no effect upon the levels of TNFα produced (179±9 pg/ml TNFα in non-adherent cell depleted OA synovial cultures of versus 178±13 pg/ml TNFα in total OA synovial cultures). Furthermore, the non-adherent cells from the OA synovial cultures were not capable, following fixation, of inducing TNFα production in normal resting monocytes (<40 pg/ml TNFα).

In summary, the results of the experiments described above indicate that $T_{ck}$ cells are involved in the induction of TNFα production by monocytes in RA synovial tissue. Hence, $T_{ck}$ cells represent a novel therapeutic target for the development of treatments of chronic inflammatory disorders.

Methods of Screening for Compounds that Selectively Target $T_{ck}$ Cells (1) Assay for NF-κB Inhibition Monocyte purification: Human peripheral blood monocytes are isolated from single donor plateletpheresis residues by Ficol/Hypaque centrifugation, as described above. Monocyte purity is then assessed by flow cytometry using fluorochrome-conjugated anti-CD45 and anti-CD14 monoclonal antibodies (Becton Dickinson, Oxford, UK), which routinely reveals that greater than 85% of cells express CD3 or CD14, respectively.

Monocyte culture: Upon isolation, monocytes are cultured in complete medium at 4×10⁶ cells/ml in 96-well culture plates (Nunc Life Technologies Ltd, Paisley, Scotland). At the start of the culture period, cells are divided into the following treatment groups:
 (i) One control group of cells is incubated in the absence of any drug challenge (negative control group);
 (ii) At least one group of cells is incubated with a test compound (a test group); and
 (iii) A final group of cells is incubated with 10 µg/ml LPS positive control group).

It will be appreciated that the concentration of the test compound in the culture medium of the test group and the duration of this initial incubation period may be varied. Typically, a range of drug concentrations and incubation duration periods will be used when testing a given compound to be tested.

Following this initial stimulatory incubation period, the monocytes are cultured for a further 18 hours at 37° C. with 5% $CO_2$ in air.

Electrophoretic mobility shift assay (EMSA): Nuclear extracts (10 µg) are prepared as described in Dent and Latchman (1993) *Transcription factors: A practical approach*, Oxford University Press. The extracts were then mixed with 5× binding buffer (100 mM Tris pH8.0, 20 mM KCl, 10 mM $MgCl_2$, 60% glycerol, 6 mM DTT), 1 µl poly(dI).poly(dC) (2.5 mg/ml) and the volume was made up to 20 µl with distilled water. After equilibration of the mixture for 5 minutes at room temperature, 5×10⁴ cpm of the following double-stranded oligonucleotide probe was added (with or without unlabelled competitor DNA):

5'-[α-$^{32}$P]dCTP-GAT CGG GAC TTT CCC-3'
3'-TCC CTG AAA GGG TAC-[α-$^{32}$P]dCTP-5'

The mixture containing the labelled probe was then left at room temperature for 20 minutes (the NF-κB promoter sequence is shown above in bold font).

Alternatively, commercially available transcription factor consensus sequence oligonucleotides may be radiolabelled and used, such as oligonucleotide E3241 (Promega). It will be appreciated that such oligonucleotides may be radiolabelled by any methods known in the art, for example by enzyme-catalysed addition of $^{32}$P-labelled dATP or dCTP.

Samples were run on a pre-electrophoresed native (0.09M Tris borate, 2 mM EDTA, pH8.0, TBE) 5% polyacrylamide gel for 90 minutes at 200 V. The gel was dried and autoradiography was performed by exposure to Hyperfilm MP (Amersham, UK). Autoradiograms were analysed by densitometry (Biorad GS670, Biorad, Watford, UK).

NF-κB inhibition is deemed to exist if the binding of NF-κB to its promoter on DNA oligonucleotides (as measured by densitometric analysis of the autoradiogram) is reduced to no more than 50% compared to the binding of nuclear extracts prepared from monocytes that have not been pre-incubated with the test compound. Preferably, the binding is no more than 20%, 10%, 5% or 1%. Ideally, the binding is substantially zero.

As a positive control in the EMSA assay (i.e. to inhibit NF-κB), monocytes may be infected with adenovirus containing IκBα (AdvIκBα) at an m.o.i. of 100:1.

Reporter gene assay: NF-κB gene expression may be measured by a reporter gene assay using a cell line stably transfected with the NF-κB gene coupled to a β-galactosidase gene, for example as described in Matilla et al. (1990) *EMBO J.* 9(13): 4425-4433.

Cells are seeded at $2\times10^6$/ml in 100 µl culture medium (RPMI 1640) containing 10% heat-inactivated foetal calf serum (BioWhittaker, Verviers, Belgium) and cultured overnight (at 37° C. in a 5% $CO_2$/95% air humidified incubator) with and without a compound to be tested. Following incubation, the cells are lysed by the addition of 20 µl 1% Triton X-100. β-galactosidase activity was assayed by adding 25 µl of 8 mg/ml chlorophenol red β-D-galactopyranoside (Boehringer Mannheim, Germany) and incubating the samples at 37° C. for 2 to 4 hours. Absorbance was measured at 574 nm on an automatic plate reader (for example, Labsystems Multiscan Bichromatic) and data were analysed with Deltasoft software (Biometallics).

NF-κB inhibition is deemed to exist if absorbance at 574 nm is reduced to no more than 50% compared to absorbance in lysates from cells which have not been incubated with the test compound. Preferably, the absorbance at 574 nm is no more than 20%, 10%, 5% or 1%. Ideally, the absorbance at 574 nm is substantially zero.

(2) Assay for PI3 Kinase Activation

PI3 kinase activity may be assayed by any method known in the art, for example using the assay described in Crawley et al (1996) *J Biol Chem* 271(27), 16357-16362, and Fukni and Hanafusa (1994) *Mol cell Biol* 9, 1651-1658.

Preferably, PI3 kinase activity is assayed as follows:

Monocyte purification: Human peripheral blood monocytes are isolated from single donor plateletpheresis residues by Ficol/Hypaque centrifugation, as described above. Monocyte purity is then assessed by flow cytometry using fluorochrome-conjugated anti-CD45 and anti-CD14 monoclonal antibodies (Becton Dickinson, Oxford, UK), which routinely reveals that greater than 85% of cells express CD3 or CD14, respectively.

Monocyte culture: Upon isolation, monocytes are cultured in complete medium at $4\times10^6$ cells/ml in 96-well culture plates (Nunc Life Technologies Ltd, Paisley, Scotland). At the start of the culture period, cells are divided into the following treatment groups:

(i) One control group of cells is incubated in the absence of any drug challenge (negative control group);

(ii) At least one group of cells is incubated with a test compound (a test group); and (iii) A final group of cells is incubated with IL-10 (100 mg/ml) for 2 minutes, as a positive control.

It will be appreciated that the concentration of the test compound in the culture medium of the test group and the duration of this initial incubation period may be varied. Typically, a range of drug concentrations and incubation duration periods will be used when testing a given compound to be tested.

Following this initial stimulatory incubation period, the PI3 kinase inhibitors wortmannin or LY294002 (Sigma, Poole, UK) are added to the monocyte cultures for 15 minutes to block PI3 kinase activation. After 18 hours in culture at 37° C. with 5% $CO_2$ in air, supernatant aliquots are harvested (200 µl/well, 3 wells/treatment group) and stored at 20° C. until used.

Immunoprecipitation and in vitro kinase assays: Following stimulation, monocytes are lysed at a density of $5\times10^6$ cells/ml in PI3 kinase lysis buffer (20 mM Tris-HCl pH7.5, 150 mM NaCl, 5 mM EDTA, 1% Nonidet-P40), supplemented with 1 mM $Na_3VO_4$, 1 mM phenylmethylsulfonyl fluoride, 1 µg/ml aprotonin, 1 µg/ml pepstatin and 10 µg/ml leukopeptin (Calbiochem). To the supernatants are added monoclonal antibodies (U5 mAbs) directed against the p85α subunit of PI3 kinase (available from Dr Cantrell, ICRF, London, UK).

After 30 minutes on ice, 20 µl of the protein G-Sepharose was added and the lysates rotated at 4° C. for 2 hours.

PI3 kinase assay: Beads containing immunoprecipitates are washed three times for 5 minutes each wash in PI3 kinase lysis buffer, once in PBS, twice in 500 mM lithium chloride, once in water and once in PI3 kinase assay buffer (40 mM Tris-HCl pH7.5, 200 mM NaCl, 1 mM EGTA). Immunoprecipitates are then resuspended in 40 µl of PI3 kinase assay buffer. Upon resuspension, 50 µl of lipid substrate mixture is added, which contains 1 mg phosphatidyl-inositol(4,5)$P_2$ (PtdIns-4,5-$P_2$) and 1 mg phosphatidylserine (PtdS) (both from Sigma, UK) made up in 2 ml of 25 mM HEPES/1 mM EDTA, and dispersed by sonication in three 15-second bursts at 4° C.). The reaction is initiated by addition of 5 µCi [γ-32P]-ATP and 100 mM ATP. The samples are incubated at room temperature for 15 minutes and the reaction quenched using 100 µl of 1 M HCl and 200 µl of 1:1 chloroform:methanol. The resultant lipid layer is then removed and dried in vacuo. The dried samples are resuspended in 50 µl chloroform, applied to a 1% oxalate-sprayed thin layer chromatography (TLC) plate and developed in propan-1-ol:2 M glacial acetic acid (65:35 v/v). Reaction products (i.e. phosphatidylinositol-3,4,5-triphosphate, PtdIns-3,4,5-$P_3$) are visualised by autoradiography using Hyperfilm MP (Amersham, UK).

PI3 kinase is deemed to have been activated if there is an increase in PI3 kinase activity (as measured by densitometric analysis of the signal corresponding to the PI3 kinase reaction product on the autoradiogram) equivalent to at least 50% of the increase induced in the IL-10 stimulated positive control group. Preferably, the increase in activity is equivalent to at least 70%, 80% or 90% of that in the positive control group. Ideally, the increase in activity is greater than that in the positive control group.

Antibodies with Specificity for $T_{ck}$ Cells

Screening Phage Display Antibody Libraries Using Whole $T_{ck}$ Cells

The selection of recombinant antibodies directly on whole cells provides a means of cloning antibodies and fragments thereof that react selectively with cell-surface antigens. A number of live cell panning methods have been developed, which can be adapted for different cell types (Winter et al, 1994, *Ann. Rev. Immunol.* 12, 433-55; De Kruif et al, 1995, *Proc. Natl. Acad. Sci. USA* 92(9), 3938-42). Selection efficiency can be greatly increased by pre-adsorbing the phage stock against cells that do not express the desired target antigen but are otherwise similar to the selection cells. Thus, the phage display library could be screened by sequential negative and positive panning against fixed or non-fixed $T_{tcr}$ (negative) and then $T_{ck}$ (positive) cells.

The following protocol is based on a method for selection of recombinant antibodies on human melanoma cells (Cai and Garen, 1995, *Proc. Natl. Acad. Sci. USA* 92(14), 6537-41). General phage display methodology is described in detail in Chapter 17 (Supplement 34) of Coligan et al (1999) In: *Current Protocols In Immunology*, Volume 3, Wiley, New York.

(i) Construct antibody phage display library from genomic cDNA prepared from peripheral blood lymphocytes of a rheumatoid arthritis patient.

(ii) Grow $T_{ck}$ cells as an attached monolayer in a 24-cm$^2$ flack until almost confluent.

(iii) Change the culture medium three times and incubate the cells for a further hour.

(iv) For the first panning step, add about $10^{11}$ pfu of the phage library in 2 ml Dubecco's minimal essential medium (DMEM)

(v) Shake flask gently for 2 hours at room temperature.

(vi) Remove medium and wash cells rapidly ten times with phosphate-buffered saline (PBS, pH7.4) at room temperature.

(vii) Elute attached phage with 2 ml elution buffer (0.1 M glycine, pH2.2, 0.1% (w/v) BSA) for 10 minutes at room temperature with gentle rocking (viii) Neutralise eluted phage immediately with 0.275 ml of 1 M Tris.Cl, pH 9.1.

(ix) Titrate phage (for example, see page 17.1.19 of Coligan et al, ibid.)

(x) Monitor the recovery of the specific recombinant antibodies (for example, see pages 17.1.26 to 17.1.28 of Coligan et al, ibid.)

(xi) Amplify phage for subsequent round of selection (for example, see pages 17.1.20 to 17.1.23 of Coligan et al, ibid.)

Therapeutic use of Compounds in the Treatment of Rheumatoid Arthritis

An amount of a compound of the invention is dissolved in sterile, non-pyrogenic water or isotonic saline. The solution is then injected intra-articularly (using a hypodermic needle) into the knee joint of a patient suffering from rheumatoid arthritis of the knee joint. Preferably, the solution is administered at regular intervals (e.g. daily, twice weekly, weekly or monthly) for a prolonged period, such that the symptoms associated with rheumatoid arthritis (e.g. inflammation of the synovium of the knee and/or joint immobility) are eased or are prevented from worsening.

It will be appreciated that the solution may be used immediately upon preparation or may be stored in sterile containers (e.g. glass ampoules) prior to use. If stored for a prolonged period, suitable preservative agents may be added to the solution.

The invention claimed is:

1. A method of identifying a compound that selectively inhibits cytokine-stimulated T cell ($T_{ck}$ cell) induced production of TNFα by monocytes at least two-fold greater than the compound inhibits T cell antigen receptor-stimulated T cell ($T_{tcr}$ cell) induced production of TNFα by monocytes
wherein said method comprises the following steps:
(a) providing a population of $T_{ck}$ cells wherein said $T_{ck}$ cells have been produced by incubating normal human peripheral blood T cells with cytokines selected from the group consisting of:
(i) IL-15;
(ii) IL-6, TNFα and IL-2; and
(iii) IL-6, TNFα and IL-15;
(b) providing a population of $T_{tcr}$ cells wherein said $T_{tcr}$ cells have been produced by incubating normal human peripheral blood T cells with one or more anti-T cell antigen receptor antibodies which activate T cell antigen receptors;
(c) incubating separate cultures of $T_{ck}$ cells and $T_{tcr}$ cells with a compound to be tested;
(d) resuspending the cultures of $T_{ck}$ cells and $T_{tcr}$ cells in the absence of the test compound;
(e) fixing the cultures of $T_{ck}$ cells and $T_{tcr}$ cells;
(f) co-culturing equal portions of each of said fixed $T_{ck}$ cells and $T_{tcr}$ cells with monocytes to allow stimulation of the monocytes; and
(g) assaying for TNFα production by said monocytes,
wherein the method identifies a compound that selectively inhibits $T_{ck}$ cell induced production of TNFα by monocytes at least two-fold greater than the compound inhibits $T_{tcr}$ cell induced production of TNFα by monocytes.

2. A method according to claim 1 wherein the compound identified is an antibody having specificity for $T_{ck}$ cells.

3. A method according to claim 1 wherein said compound has efficacy in the treatment of rheumatoid arthritis.

4. A method according to claim 1 wherein said anti-T cell antigen receptor antibody is an anti-CD3 antibody.

* * * * *